(12) United States Patent
Cooper et al.

(10) Patent No.: US 7,419,601 B2
(45) Date of Patent: Sep. 2, 2008

(54) NANOMESH ARTICLE AND METHOD OF USING THE SAME FOR PURIFYING FLUIDS

(75) Inventors: Christopher H. Cooper, Windsor, UT (US); Alan G. Cummings, So Woodstock, UT (US); Mikhail Y. Starostin, Hanover, NH (US); Charles P. Honsinger, Windsor, UT (US)

(73) Assignee: Seldon Technologies, LLC, Windsor, VT (US)

( * ) Notice: Subject to any disclaimer, the term of this patent is extended or adjusted under 35 U.S.C. 154(b) by 203 days.

(21) Appl. No.: 11/111,736

(22) Filed: Apr. 22, 2005

(65) Prior Publication Data

US 2005/0263456 A1     Dec. 1, 2005

Related U.S. Application Data

(63) Continuation-in-part of application No. 10/794,056, filed on Mar. 8, 2004, now Pat. No. 7,211,320.

(60) Provisional application No. 60/452,530, filed on Mar. 7, 2003, provisional application No. 60/468,109, filed on May 6, 2003, provisional application No. 60/499,375, filed on Sep. 3, 2003.

(51) Int. Cl.
*C02F 1/42* (2006.01)
*B01D 53/02* (2006.01)

(52) U.S. Cl. .............. 210/679; 210/748; 210/688; 210/683; 210/685; 210/687; 210/691; 977/700; 95/132; 95/133; 95/134; 95/138; 95/143; 95/903; 95/57; 95/81; 95/90

(58) Field of Classification Search ............... 977/700; 210/748, 660, 681, 688, 683, 685, 687, 691, 210/679; 95/132–134, 903, 138, 57, 143, 95/81, 90
See application file for complete search history.

(56) References Cited

U.S. PATENT DOCUMENTS

| | | | |
|---|---|---|---|
| 5,424,054 | A | 6/1995 | Bethune et al. |
| 5,458,784 | A | 10/1995 | Baker et al. |
| 5,691,054 | A | 11/1997 | Tennent et al. |
| 5,698,175 | A | 12/1997 | Hiura et al. |
| 5,800,706 | A | 9/1998 | Fischer |

(Continued)

FOREIGN PATENT DOCUMENTS

EP        1 092 680 A1     4/2001

(Continued)

OTHER PUBLICATIONS

European Search Report for EP 07014878, 2007.

*Primary Examiner*—Chester T Barry
(74) *Attorney, Agent, or Firm*—Finnegan, Henderson, Farabow, Garrett & Dunner

(57) ABSTRACT

Disclosed herein are articles for removing contaminants from a fluid, such as a liquid or gas, the article comprising carbon nanotubes, which comprise at least one molecule or cluster attached thereto or located therein, wherein the carbon nanotubes are present in the article in an amount sufficient to reduce the concentration of contaminants in fluid that come into contact with the article. A method of making the nanomesh material used in such articles is also disclosed, as are methods of purifying fluids using these articles.

72 Claims, 22 Drawing Sheets

Body of Carbon Nanotube

U.S. PATENT DOCUMENTS

| | | |
|---|---|---|
| 5,846,658 A | 12/1998 | Tennent et al. |
| 5,968,650 A | 10/1999 | Tennent et al. |
| 5,985,112 A | 11/1999 | Fischer |
| 6,090,363 A | 7/2000 | Green et al. |
| 6,099,960 A | 8/2000 | Tennent et al. |
| 6,099,965 A | 8/2000 | Tennent et al. |
| 6,113,819 A | 9/2000 | Tennent et al. |
| 6,157,043 A | 12/2000 | Miyamoto |
| 6,203,814 B1 | 3/2001 | Fisher et al. |
| 6,331,265 B1 | 12/2001 | Dupire et al. |
| 6,333,016 B1 | 12/2001 | Resasco et al. |
| 6,346,136 B1 | 2/2002 | Chen et al. |
| 6,346,189 B1 | 2/2002 | Dai et al. |
| 6,350,488 B1 | 2/2002 | Lee et al. |
| 6,413,487 B1 | 7/2002 | Resasco et al. |
| 6,420,293 B1 | 7/2002 | Chang et al. |
| 6,432,177 B1 | 8/2002 | Dallas et al. |
| 6,432,866 B1 | 8/2002 | Tennent et al. |
| 6,455,021 B1 | 9/2002 | Saito |
| 6,468,930 B2 | 10/2002 | Kruszewski |
| 6,471,936 B1 | 10/2002 | Chen et al. |
| 6,495,116 B1 | 12/2002 | Herman |
| 6,495,258 B1 | 12/2002 | Chen et al. |
| 6,511,527 B2 | 1/2003 | Yang et al. |
| 6,514,413 B2 | 2/2003 | Pimenov et al. |
| 6,521,321 B2 | 2/2003 | Kahlbaugh et al. |
| 6,536,605 B2 | 3/2003 | Rice et al. |
| 6,538,262 B1 | 3/2003 | Crespi et al. |
| 6,673,136 B2 | 1/2004 | Gillingham et al. |
| 6,673,392 B2 | 1/2004 | Lee et al. |
| 6,692,715 B2 | 2/2004 | Barbeau |
| 6,702,875 B2 | 3/2004 | Jagtoyen et al. |
| 6,713,519 B2 | 3/2004 | Wang et al. |
| 6,746,469 B2 | 6/2004 | Mouw |
| 6,749,826 B2 | 6/2004 | Tillotson et al. |
| 6,797,167 B2 | 9/2004 | Koslow |
| 6,818,821 B2 | 11/2004 | Fujieda et al. |
| 6,824,689 B2 | 11/2004 | Wang et al. |
| 6,838,005 B2 | 1/2005 | Tepper et al. |
| 6,841,075 B2 | 1/2005 | Penth et al. |
| 6,852,219 B2 | 2/2005 | Hammond |
| 6,921,575 B2 | 7/2005 | Horiuchi et al. |
| 6,967,013 B2 | 11/2005 | Someya et al. |
| 7,014,952 B2 | 3/2006 | Shiraishi et al. |
| 7,105,596 B2 | 9/2006 | Smalley et al. |
| 7,138,100 B2 | 11/2006 | Smalley et al. |
| 7,214,360 B2 | 5/2007 | Chen et al. |
| 7,250,074 B2 * | 7/2007 | Tonkovich et al. ............ 95/130 |
| 2001/0003082 A1 | 6/2001 | Kahlbaugh et al. |
| 2001/0024633 A1 | 9/2001 | Lee et al. |
| 2002/0023874 A1 | 2/2002 | Penth et al. |
| 2002/0056686 A1 | 5/2002 | Kyrlidis et al. |
| 2002/0063093 A1 | 5/2002 | Rice et al. |
| 2002/0085968 A1 | 7/2002 | Smalley et al. |
| 2002/0092613 A1 | 7/2002 | Kuper |
| 2002/0106958 A1 | 8/2002 | Kruszewski |
| 2002/0136683 A1 | 9/2002 | Smalley et al. |
| 2002/0148776 A1 | 10/2002 | Cousart et al. |
| 2002/0150524 A1 | 10/2002 | Smalley et al. |
| 2002/0167782 A1 | 11/2002 | Andelman et al. |
| 2002/0172639 A1 | 11/2002 | Horiuchi et al. |
| 2002/0193030 A1 | 12/2002 | Yao et al. |
| 2003/0000538 A1 | 1/2003 | Bereman |
| 2003/0020024 A1 | 1/2003 | Ferain et al. |
| 2003/0024884 A1 | 2/2003 | Petrikh |
| 2003/0029718 A1 | 2/2003 | Faris |
| 2003/0037675 A1 | 2/2003 | Gillingham et al. |
| 2003/0042205 A1 | 3/2003 | Gaudet et al. |
| 2003/0044339 A1 | 3/2003 | Barbeau |
| 2003/0075682 A1 | 4/2003 | Colbert et al. |
| 2003/0082979 A1 | 5/2003 | Bean et al. |
| 2003/0092342 A1 | 5/2003 | Tennent et al. |
| 2003/0098518 A1 | 5/2003 | Averdung et al. |
| 2003/0102222 A1 | 6/2003 | Zhou et al. |
| 2003/0111404 A1 | 6/2003 | Koslow |
| 2003/0116503 A1 | 6/2003 | Wang et al. |
| 2003/0118727 A1 | 6/2003 | Ting et al. |
| 2003/0118907 A1 | 6/2003 | Shiraishi et al. |
| 2003/0119034 A1 | 6/2003 | Kang et al. |
| 2003/0127393 A1 | 7/2003 | Tepper et al. |
| 2003/0129119 A1 | 7/2003 | Chiu et al. |
| 2003/0129122 A1 | 7/2003 | Chen et al. |
| 2003/0147801 A1 | 8/2003 | Someya et al. |
| 2003/0147802 A1 | 8/2003 | Smalley et al. |
| 2003/0148086 A1 | 8/2003 | Pfefferle et al. |
| 2003/0154865 A1 | 8/2003 | Zornes |
| 2003/0155143 A1 | 8/2003 | Fujieda et al. |
| 2003/0164427 A1 | 9/2003 | Glatkowski et al. |
| 2003/0180472 A1 | 9/2003 | Zhou et al. |
| 2003/0181328 A1 | 9/2003 | Hwang et al. |
| 2003/0215903 A1 | 11/2003 | Hyman et al. |
| 2003/0217928 A1 | 11/2003 | Lin et al. |
| 2004/0007528 A1 | 1/2004 | Bakajin et al. |
| 2004/0118285 A1 | 6/2004 | Kim et al. |
| 2004/0118287 A1 | 6/2004 | Jaffe et al. |
| 2004/0131881 A1 | 7/2004 | Zheng et al. |
| 2004/0173506 A1 | 9/2004 | Doktycz et al. |
| 2004/0178135 A1 | 9/2004 | Beplate |
| 2004/0251122 A1 | 12/2004 | Goswami |
| 2004/0256311 A1 | 12/2004 | Extrand |
| 2005/0040090 A1 | 2/2005 | Wang et al. |
| 2005/0067346 A1 | 3/2005 | Noack et al. |
| 2005/0074479 A1 | 4/2005 | Weber et al. |
| 2005/0096509 A1 | 5/2005 | Olson |
| 2005/0150832 A1 | 7/2005 | Tsukamoto |

FOREIGN PATENT DOCUMENTS

| | | |
|---|---|---|
| EP | 1 439 147 A | 7/2004 |
| JP | 2003 181288 A | 7/2003 |
| JP | 2004 066009 | 3/2004 |
| JP | 2004 148305 | 5/2004 |
| WO | WO 97/32571 | 9/1997 |
| WO | WO 2004/080578 | 9/2004 |
| WO | WO 2005/001021 A | 1/2005 |
| WO | WO 2005/005687 | 1/2005 |

* cited by examiner

Body of Carbon Nanotube

Filled Carbon Nanotube

Section of Carbon Nanotube with Dopants

Figure 10: Ionic shielding (DeBye Atmosphere) in a water solutions

Figure 11: Flow chart of the process used to manufacture fluid purification article.

Flat design of the Carbon Nanotube Fluid Purification Device

Contaminated fluid enters through the inlet hole, passes through the membrane and comes out the outlet hole purified.

Figure 18: Schematic representation of nanomesh deposition station for a cylindrical fluid purification device.

Figure 21: Schematic of the cylindrical wind tunnel used for Air Membrane testing.

NANOMESH ARTICLE AND METHOD OF USING THE SAME FOR PURIFYING FLUIDS

This is a continuation-in-part of U.S. patent application Ser. No. 10/794,056, filed Mar. 8, 2004, now U.S. Pat. No. 7,211,320, and claims the benefit of domestic priority to U.S. Provisional Patent Application Ser. No. 60/452,530 filed Mar. 7, 2003, U.S. Provisional Patent Application Ser. No. 60/468,109 filed May 6, 2003, and U.S. Provisional Patent Application Ser. No. 60/499,375 filed Sep. 3, 2003, all of which are herein incorporated by reference in their entirety.

The present disclosure relates to an article for removing contaminants from a fluid, such as a liquid or gas, wherein the article comprises carbon nanotubes. The present disclosure also relates to methods of making such an article as well as methods of removing contaminants from fluid using the article. In certain embodiments, the disclosed article is used to produce potable water from waters contaminated with microorganisms or to desalinate salt water.

There are many procedures and processes to treat fluids for consumption, use, disposal, and other needs. Among the most prevalent procedures are chemical treatments to sterilize water, distillation to purify liquids, centrifugation and filtration to remove particulates (in both liquid and air), decanting to separate two phases of fluids, reverse osmosis and electrodialysis to de-ionize liquids, pasteurization to sterilize foodstuffs, and catalytic processes to convert undesirable reactants into useful products. Because each of these methods is designed for specific applications, a combination of methods is typically needed to achieve a final product.

Factors to be balanced when treating fluids include the rate of fluid flow, the flow resistance and level of contaminant removal. It would be desirable to have a material that could balance the first two factors, while achieving a higher level of contaminant removal than previously possible.

The promise of nanotechnology materials is that they will enable us to do things not possible with more traditional macro-scale materials, such as fluid purification. Many of the current processes can be improved by using articles or filters comprising nanomaterial, such as carbon nanotubes. It has been discovered that a mesh including carbon nanotubes (a "nanomesh"), properly prepared, can be used to remove a myriad of contaminants from fluid, including viruses, bacteria, organic and inorganic contaminants, salt ions, nano- or micron size particulates, chemicals (both natural and synthetic), while achieving at least one additional benefit, such as maintaining or improving the rate of fluid flow through the article, decreasing the flow resistance across the article or lowering the weight of the resulting article.

As used herein, the term "nano" refers to a material or structure whose size is on a scale around one billionth of a meter (i.e., nm), such as on the molecular level. For example, the term "nanotechnology" generally refers to technology that in at least one dimension has a size scale of 1 to 500 nm, such as 1 to 100 nm, exhibits at least one property or function as a result of the small scale, and is able to control or manipulate individual atoms or molecules.

SUMMARY OF INVENTION

To achieve the foregoing, there is provided an article generally comprised of carbon nanotubes, where at least one carbon nanotube is attached or connected to another carbon nanotube, or to other materials, such as fibers, particles or a substrate. "Carbon nanotube(s)" refer to a nanoscale tubular structure(s) composed of six-member rings of carbon whose bonding patterns create a hexagonal lattice which closes upon itself to form the walls of the cylindrical structure. The interconnected structure which is at least partially comprised of nanotubes is referred to herein as a "nanomesh".

Disclosed herein is an article for removing contaminants from a fluid, such as water or air. The article generally comprises carbon nanotubes and may or may not include at least one molecule or cluster attached thereto or located therein, wherein the carbon nanotubes are present in the article in an amount sufficient to reduce the concentration of the contaminants in fluid that come into contact with the article.

There is also provided a method of reducing the amount of contaminants in a fluid, the method comprising contacting the fluid with the article as described herein for a time sufficient to separate, remove, immobilize, modify or destroy at least one contaminant from the fluid. In one embodiment, the method may be used to remove contaminants from water or the air.

There is further provided a method of preparing a nanomesh material comprising carbon nanotubes. The method comprises mechanical, chemical or irradiative treatments, or any combination thereof, of carbon nanotubes in a medium sufficient to attach at least one functional chemical group to a surface of the carbon nanotube, thereby forming functionalized carbon nanotubes. The method further comprises rinsing and/or dispersing the functionalized carbon nanotubes in at least one solvent chosen from aqueous, inorganic, and organic solvents. The method further comprises combining multiple types of carbon nanotubes that may have different chemical functionalization, to assist in the removal, destruction, or modification of contaminants.

In one embodiment, the method further comprises mixing the functionalized carbon nanotubes with fibers and at least one solvent to form a suspension of functionalized carbon nanotubes and fibers. A nanomesh layer is formed, typically on a porous substrate, by depositing the suspension on the substrate by any standard method, such as vacuum filtration.

Aside from the subject matter discussed above, the present disclosure includes a number of other exemplary features such as those explained hereinafter. It is to be understood that both the foregoing description and the following description are exemplary only.

BRIEF DESCRIPTION OF THE DRAWINGS

The accompanying figures are incorporated in, and constitute a part of this specification.

and a higher frequency AC signal (to disrupt the DeBye atmosphere) imposed across the series of nanomesh membranes.

Figure 10:
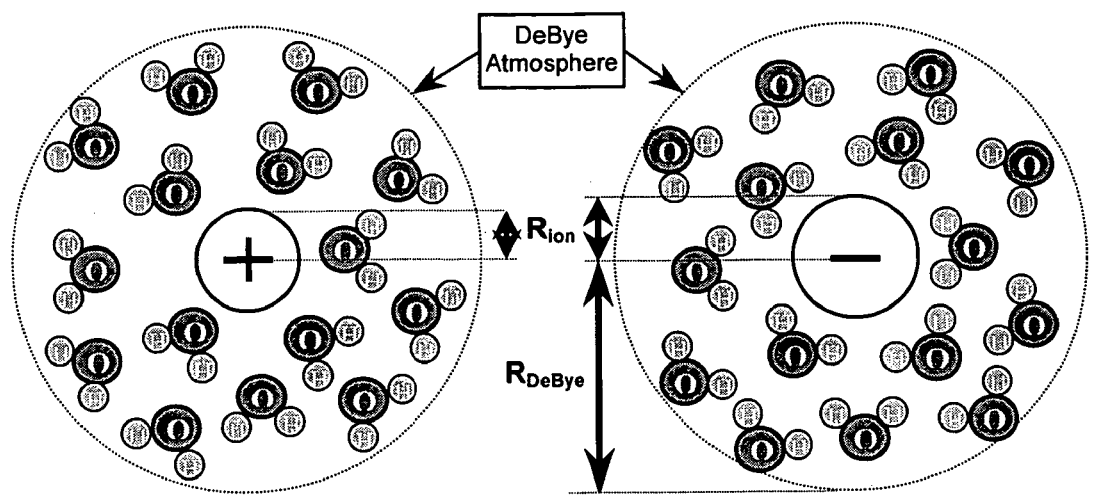

FIG. 10 schematically demonstrates the neighborhood of ions in a water solution and shows the shielding of charges by the formation of a molecular cloud (DeBye atmosphere) due to the polarized nature of the water molecule.

Figure 11:
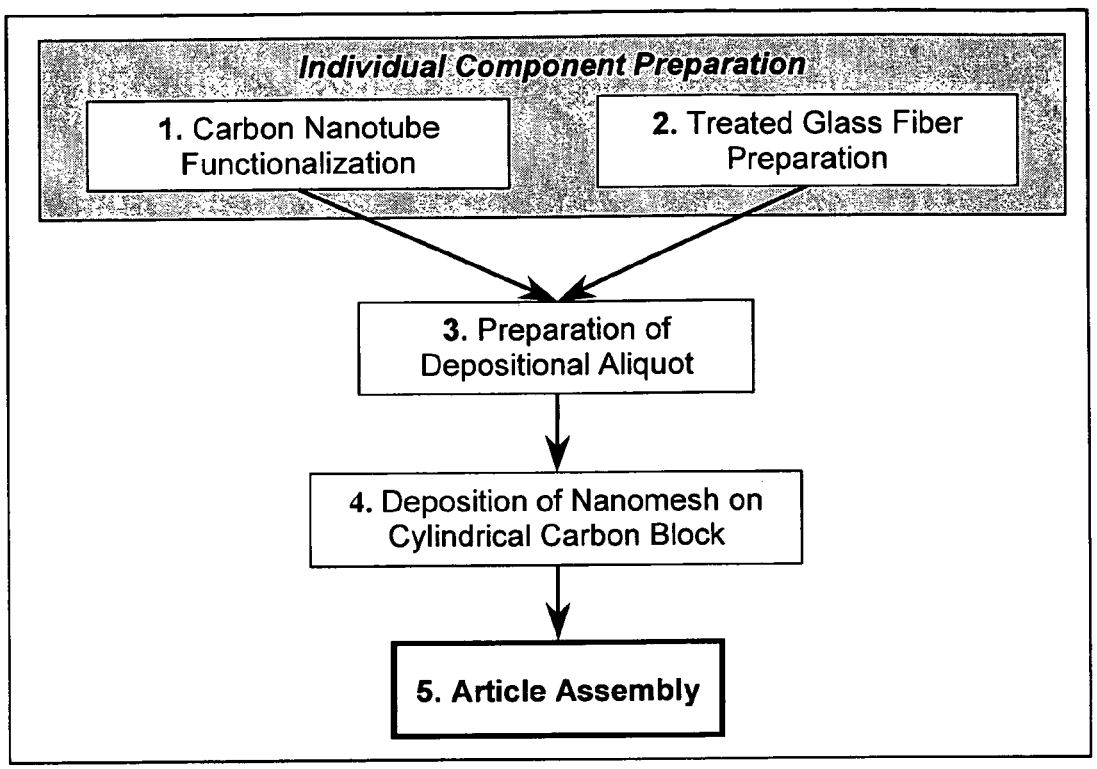

FIG. 11 is a flow chart for the process used to manufacture fluid purification devices. This example is specific to the cylindrical substrate, but can be easily generalized to any shape article using any substrate and fiber and/or particle in solution.

Figure 12:
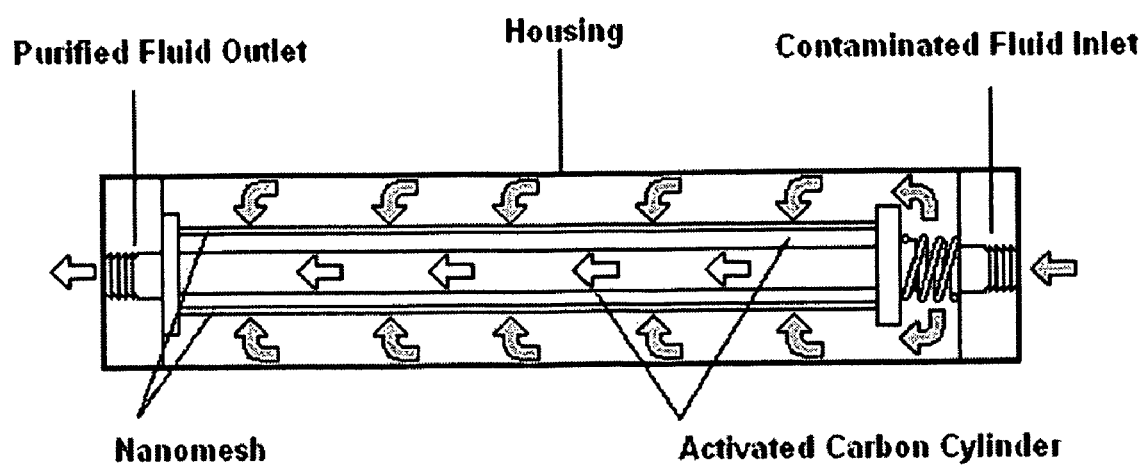

FIG. 12 represents the structure of a cylindrical version of the inventive fluid purification article.

Figure 13:
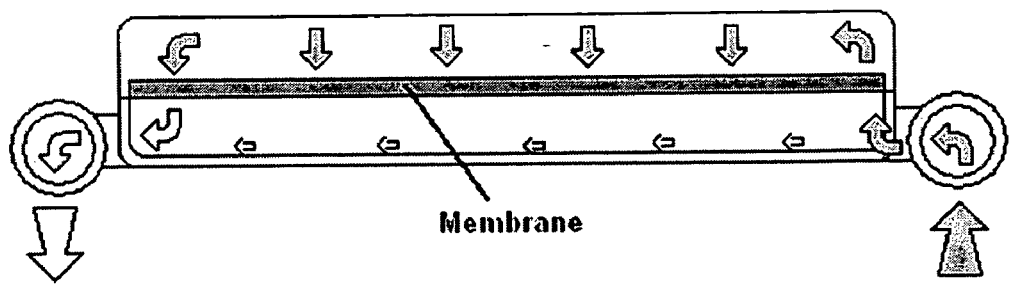

FIG. 13 represents a flat version of the inventive fluid purification article.

Figure 14:

FIG. 14 is a light microscope image showing nearly uniform bacterial (stained) coverage for untreated solution in Example #1, sample #1.

Figure 15:
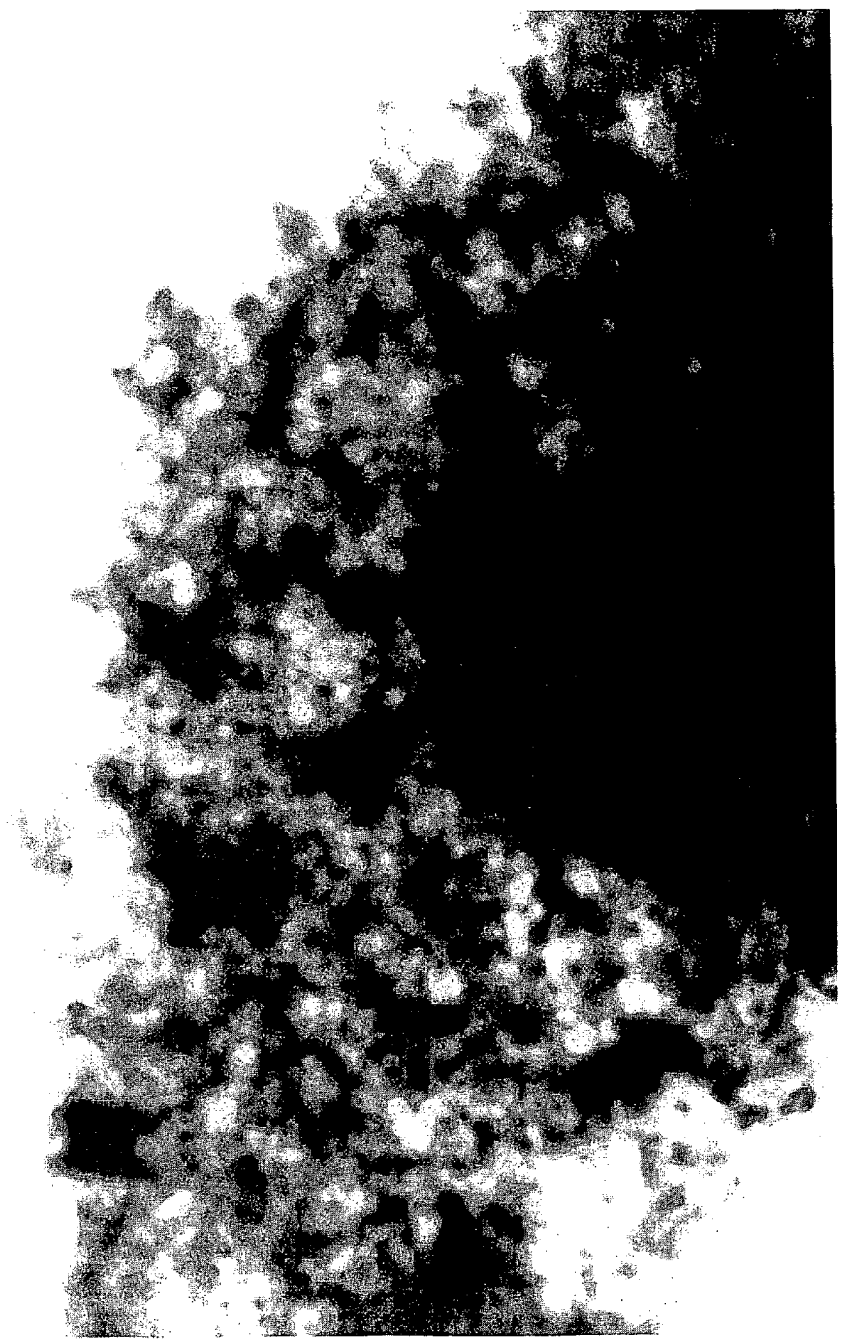
Figure 1C:
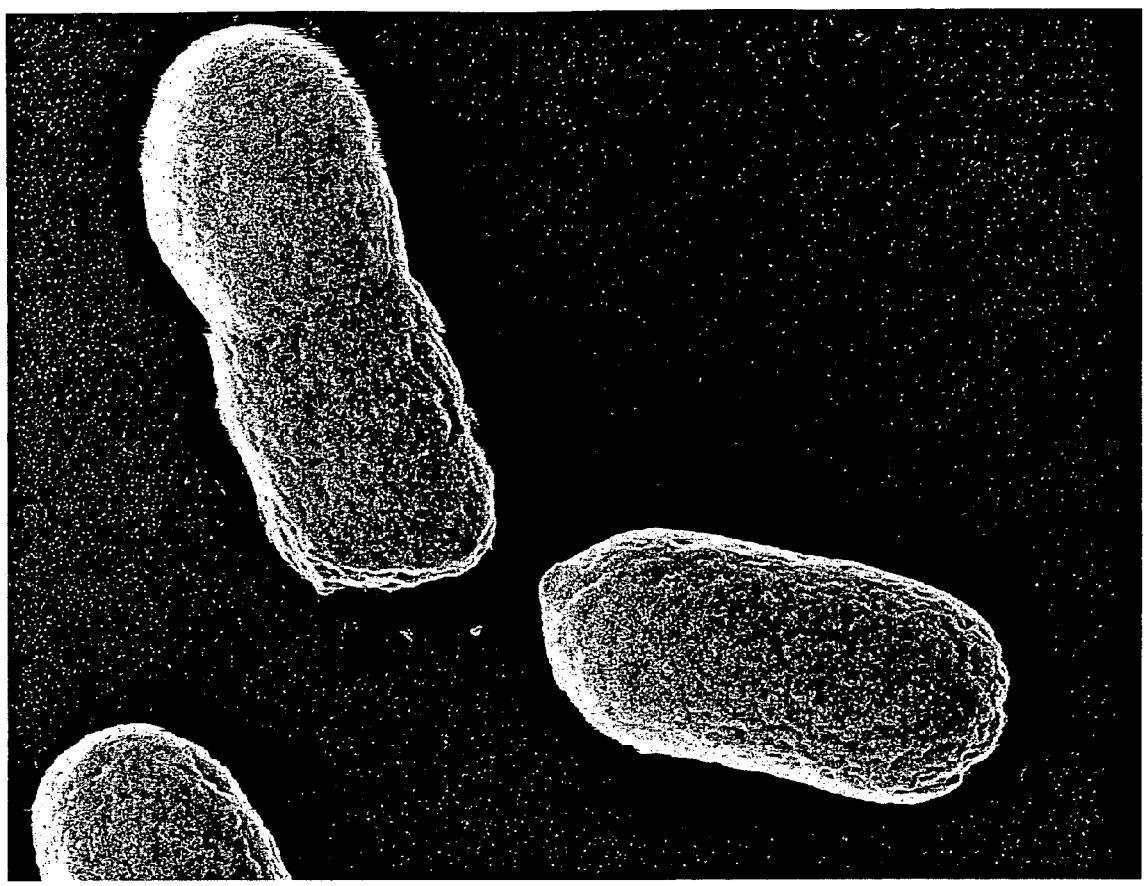

FIG. 15 is a light microscope image showing bacteria (stained) clumped on carbon nanotubes in the nanotube treated solution in Example #1, sample #2.

FIG. 16 is a Scanning Electron Microscope (SEM) image showing bacteria with normal cell walls in the absence of nanotubes from Example #1, sample #1.

Figure 17:
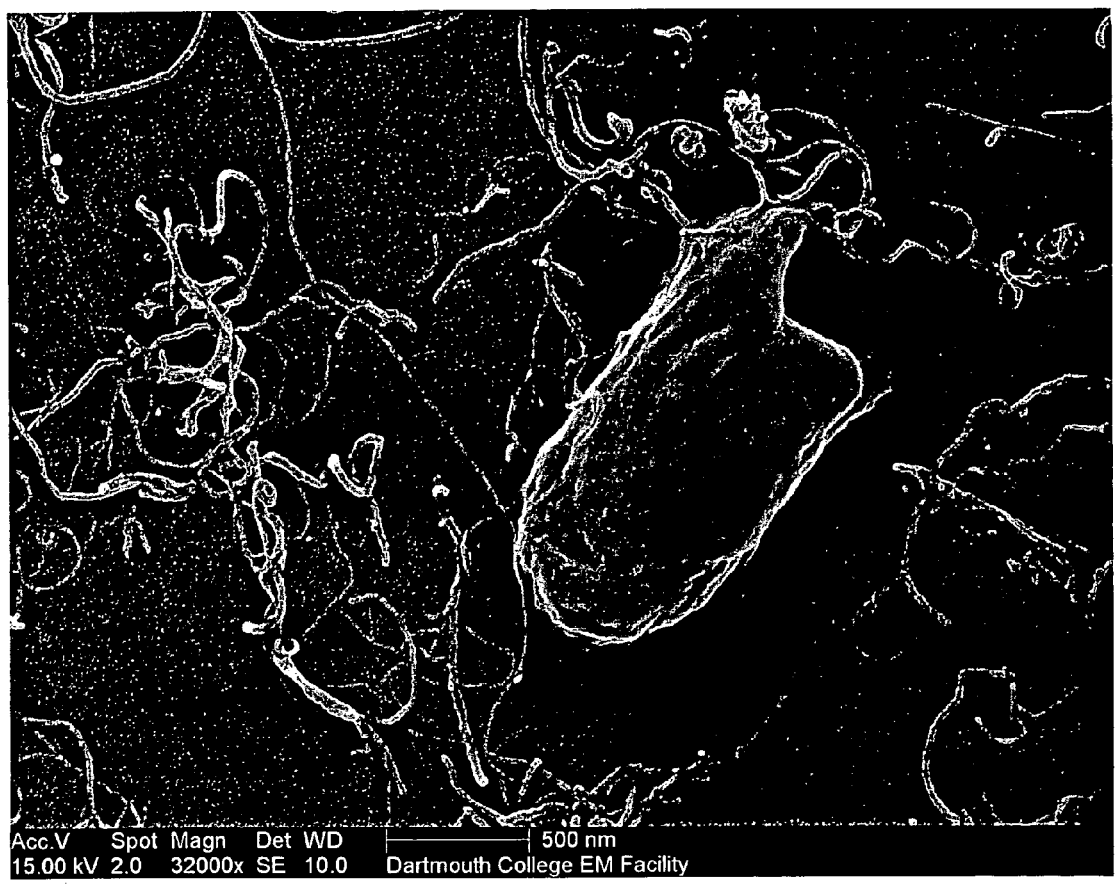

FIG. 17 is an SEM image showing the diffuse and damaged cell wall of a bacteria that has interacted with the nanotubes (in Example #1, sample #2) which suggests that this interaction is capable of destruction of the bacterial cell.

Figure 18:
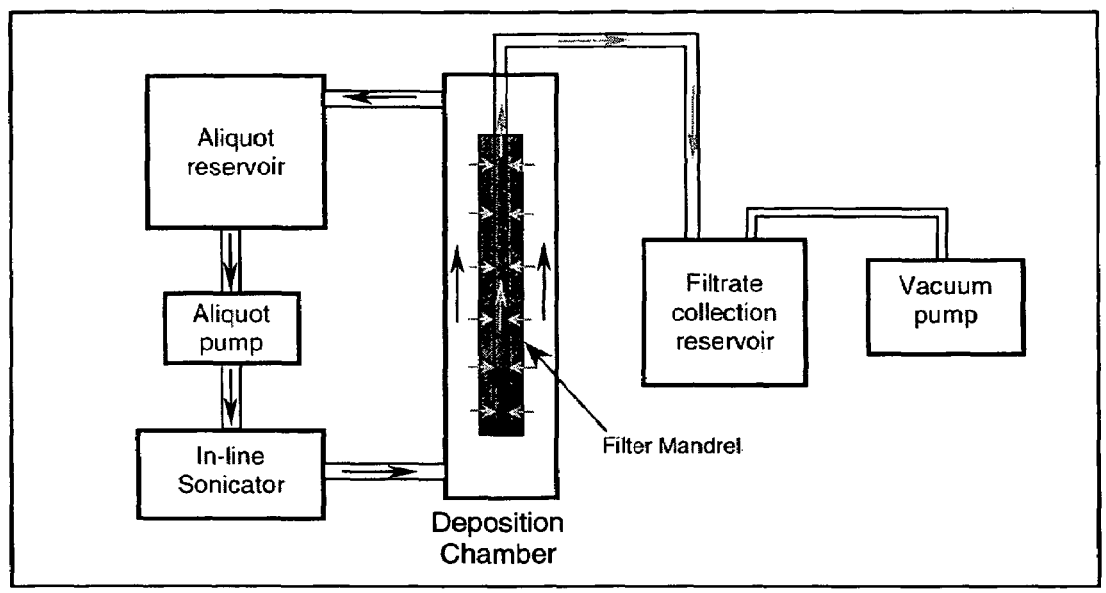

FIG. 18 is a schematic of the deposition apparatus for creating a nanomesh on a cylindrical shaped substrate.

Figure 19:
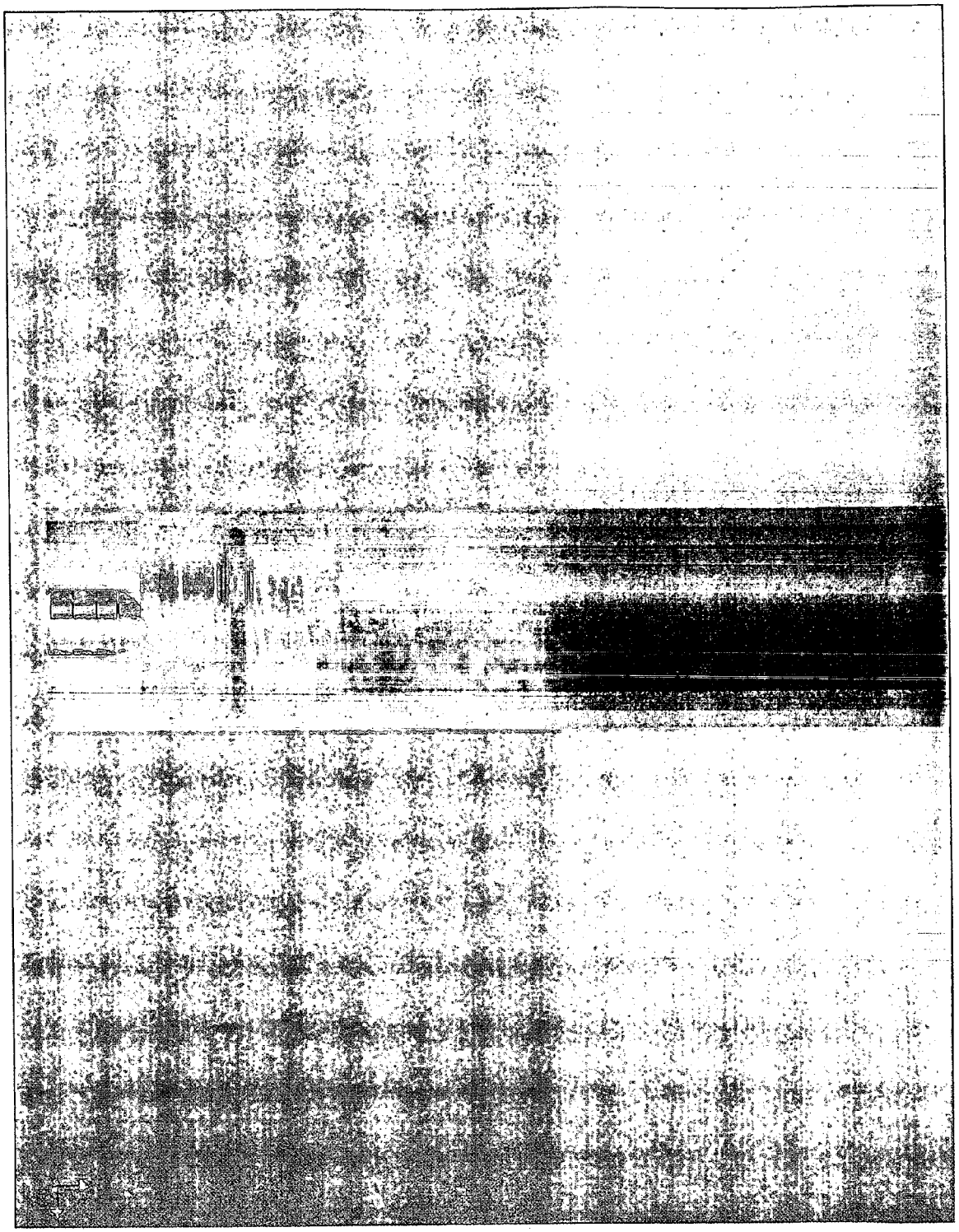

FIG. 19 is a diagram showing an assembled cylindrical fluid purification article.

Figure 20:
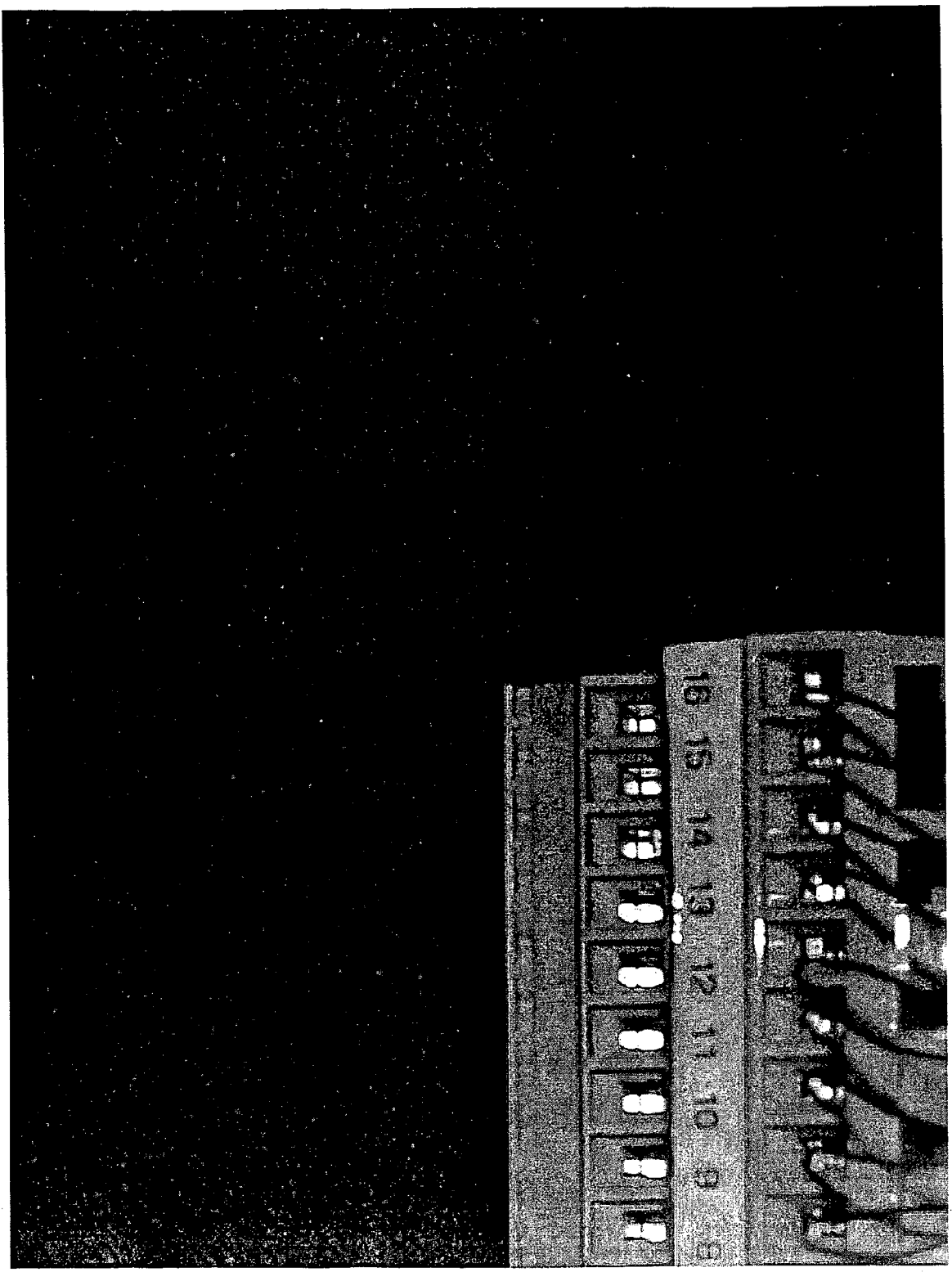

FIG. 20 is a photograph of a test desalination device.

FIG. 21 is a schematic representation of the air membrane testing apparatus.

Figure 22:
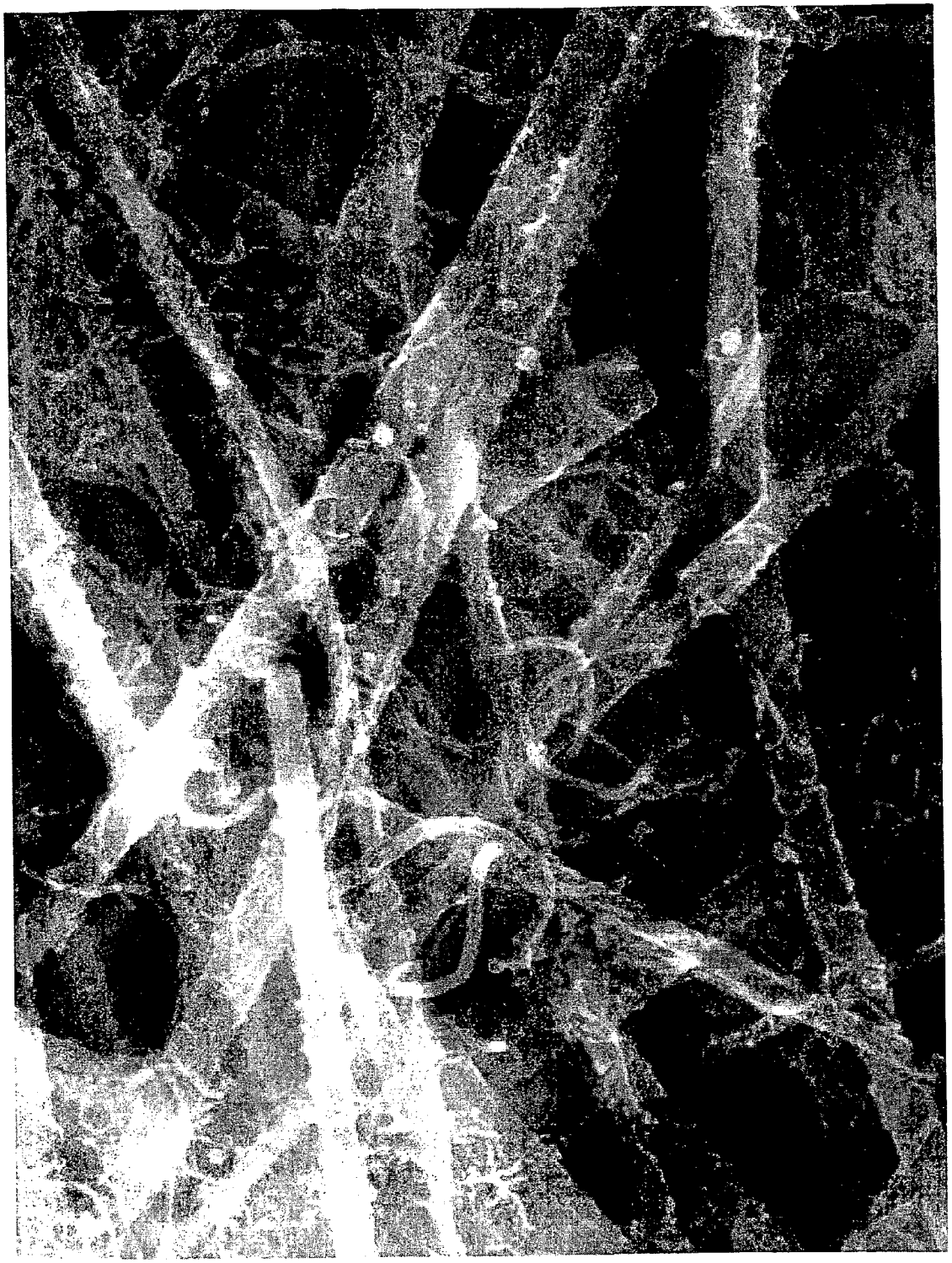

FIG. 22 is a SEM micrograph of the self-assembled carbon nanotube/glass fiber nanomesh.

DETAILED DESCRIPTION OF INVENTION

There is provided in one aspect of the present disclosure an article for removing contaminants from a fluid. "Fluid" is intended to encompass liquids or gases. "Contaminants" means at least one unwanted or undesired element, molecule or organism in the fluid. "Removing" (or any version thereof) is understood to mean destroying, modifying, or separating contaminants using at least one of the following mechanisms: particle size exclusion, absorption, adsorption, chemical or biological interaction or reaction. "Chemical or biological interaction or reaction" is understood to mean an interaction with the contaminant through either chemical or biological processes that renders the contaminant incapable of causing harm. Examples of this are reduction, oxidation, chemical denaturing, physical damage to microorganisms, bio-molecules, ingestion, and encasement.

"Particle size" is defined by a number distribution, e.g., by the number of particles having a particular size. The method is typically measured by microscopic techniques, such as by a calibrated optical microscope, by calibrated polystyrene beads, by calibrated scanning probe microscope scanning electron microscope, or optical near field microscope. Methods of measuring particles of the sizes described herein are taught in Walter C. McCrone's et al., *The Particle Atlas*, (*An encyclopedia of techniques for small particle identification*), Vol. I, Principles and Techniques, Ed. 2 (Ann Arbor Science Pub.), which are herein incorporated by reference.

Non-limiting examples of liquids that may be cleaned using the article described herein include water, foodstuffs, biological fluids, petroleum and its byproducts, non-petroleum fuels, medicines, organic and inorganic solvents, and the liquid forms of hydrogen, oxygen, nitrogen and carbon dioxide, as may be used for rocket propellants or in industrial applications.

Non-limiting examples of foodstuffs that can be treated with this article comprise animal by-products (such as eggs and milk), fruit juice, alcoholic and nonalcoholic beverages, natural and synthetic syrups, and natural and synthetic oils used in the cooking or food industry [such as olive oil, peanut oil, flower oils (sunflower, safflower), vegetable oil, or oils derived from animal sources (i.e. butter, lard)], or any combination thereof. As one example, sulfites are often added to wine to prevent discoloration and aid in preservation. However, sulfites raise health concerns and should be avoided. One aspect of the present invention could include the targeted removal of sulfites upon dispensing, benefiting the wine industry from the purification process described herein.

Biological fluids that may be decontaminated with the article described herein could be generally derived from an animal, human, plant, or comprise a culture/growth broth used in the processing of a biotechnology or pharmaceutical product. In one embodiment, the biological fluids which may be cleaned comprise blood (or blood components), serums, and milk. Biological reagents used in pharmaceutical products are often quite labile and difficult to sterilize by conventional techniques. Removal of small microorganisms (such as *Mycoplasma* and viruses) cannot be accomplished by conventional filtration. The inventive carbon nanomesh article may be used for viral removal without causing damage to the serum proteins often present and needed in biological reagents. In one embodiment, the physical and chemical properties of the nanomesh can be controlled to enable removal of contaminants that are created during drug fabrication.

In another embodiment, the inventive article can be used for the sterilization of petroleum products. A significant contamination problem is the latent growth of bacteria in petroleum or its derivatives during storage, which has been a problem particularly with aviation fuel. The presence of such bacteria can severely foul and eventually ruin the fuel. Accordingly, a major area of concern in the area of liquid purification is the cleaning bacteria from natural and/or synthetic petroleum products. Natural and/or synthetic petroleum and its byproducts include aviation, automotive, marine, locomotive, and rocket fuels, industrial and machine oils and lubricants, and heating oils and gases.

Another significant contaminant issue with petroleum products is high sulfur content and excessive levels of certain metals, a notable example being lead. Government regulations prohibit sulfur and lead concentrations in hydrocarbon fuels (used in internal combustion engines) in excess of specific amounts (MCL—maximum contamination level). Accordingly, there is a need for an article to remove specific chemical contaminants from petroleum without adding other unwanted constituents. In one embodiment, the article described herein can be used to remove sulfur and/or specific metals from hydrocarbon or other types of fuel, such as gases used in fuel cells.

As many of the foregoing contaminants may be dispersed in air, there is a need for an article for cleaning gases. Accordingly, another aspect of the present invention includes a method of cleaning the air to remove any of the previously listed contaminants. Non-limiting examples of gases that may be cleaned using the article described herein include one or more gases chosen from the air or exhausts from vehicles, smoke stacks, chimneys, or cigarettes. When used to clean air, the article may take a flat form to provide a greater surface area for air flow. Such flat shapes provide the additional benefit of being able to be easily cut into appropriate shapes for various filter designs, such as those used in gas masks, as well as HVAC systems. The following gases that may be treated according to the present disclosure, such as scrubbed to clean the gas or remove them from exhaust, include argon, acetylene, nitrogen, nitrous oxide, helium, hydrogen, oxygen, ammonia, carbon monoxide, carbon dioxide, propane, butane, natural gas, ethylene, chlorine, or mixtures of any of the foregoing, such as air, nitrogen oxide, and gases used in diving applications, such as Helium/Oxygen mixtures.

Further, it should be noted that what might be identified as a contaminant in one fluid application may actually be a desired product in another. For example, the contaminant may contain precious metals or a beneficial pharmaceutical product. Therefore, in one embodiment, it may be beneficial to separate, retain and collect the contaminants rather than just removing and destroying them. The ability to "catch and release" desired contaminants, enabling the isolation of useful contaminants or certain reaction byproducts, may be accomplished by tuning the zeta potential and/or utilizing nano-electronic control of the nanomesh article, as described in more detail below.

Applications for the articles described herein include home (e.g. domestic water and air filtration), recreational (environmental filtration), industrial (e.g. solvent reclamation, reactant purification), governmental (e.g. the Immune Building Project, military uses, waste remediation), and medical (e.g. operating rooms, clean air and face masks) locations.

Figure 1:
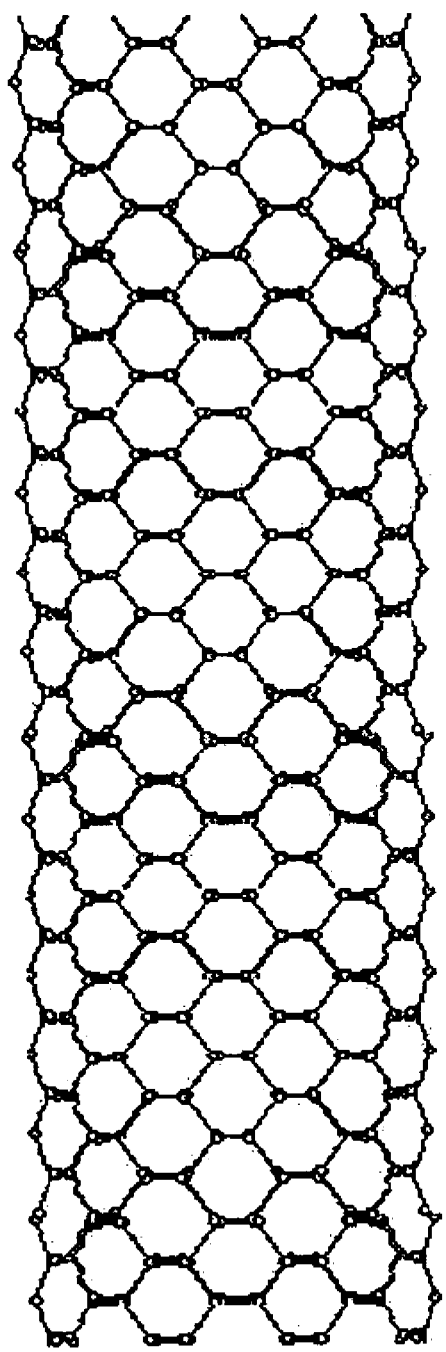
FIG. 1 is a schematic representation of the bonding structure and shape of a single walled carbon nanotube.

Carbon nanotubes generally have two forms: single wall and multi walls. Single-wall carbon nanotubes comprises one of these tubular structures so that the inter-connected hexagons line-up with each other. FIG. 1 depicts a single walled carbon nanotube. In one embodiment, these single-walled nanotubes are generally around 1-2 nm in diameter, similar to human DNA (~2 nm), and usually range from hundreds of nanometers to many microns in length. Multi-walled carbon nanotubes comprise many concentric shells of these tubular structures. They can have diameters of tens of nanometers, and can theoretically have lengths up to hundreds of meters.

While not necessary, the nanomesh described herein can comprise carbon nanotubes attached to each other, or to another material. The attachment and/or connection within the nanomesh is a result of forces acting at the nanoscale, non-limiting examples of which are Van der Waals forces, covalent bonding, ionic bonding, geometric constraints, electrostatic, magnetic, electromagnetic, or Casimir forces or combinations thereof.

The present disclosure also relates to a method of purifying fluid by contacting contaminated fluid with the nanomesh in the article described herein. In one embodiment, the method of purifying fluid comprises contacting the fluid with a nanomesh, wherein the carbon nanotubes are present in the nanomesh in an amount sufficient to reduce the concentration of at least one contaminant in the fluid that comes into contact with the nanomesh or the interaction zone created by the nanomesh. As used herein "reduce the concentrations of at least one contaminant," means a reduction of at least one contaminant to a level below that of the untreated fluid, such as below the maximum contamination levels (MCL) as defined by appropriate regulatory agencies or industrial requirements governing the quality standards of the particular fluid after being treated with the inventive article.

One aspect of the present disclosure is related to the use of carbon nanotubes that have a scrolled tubular or non-tubular nano-structure of carbon rings. These carbon nanotubes are usually single-walled, multi-walled or combinations thereof, and may take a variety of morphologies. For example, the carbon nanotubes used in the present disclosure may have a morphology chosen from horns, spirals, multi-stranded helicies, springs, dendrites, trees, spider nanotube structures, nanotube Y-junctions, and bamboo morphology. Some of the above described shapes are more particularly defined in M. S. Dresselhaus, G. Dresselhaus, and P. Avouris, eds. Carbon Nanotubes: Synthesis, Structure, Properties, and Applications, *Topics in Applied Physics.* 80. 2000, Springer-Verlag; and "A Chemical Route to Carbon Nanoscrolls, Lisa M. Viculis, Julia J. Mack, and Richard B. Kaner; *Science,* 28 Feb. 2003; 299, both of which are herein incorporated by reference.

In one aspect of the disclosed article, a majority of the carbon nanotubes are distorted by crystalline defects such that they exhibit a greater purification performance than non-distorted carbon nanotubes. "Crystalline defects" refers to sites in the tube walls of carbon nanotubes where there is a lattice distortion in at least one carbon ring.

Figure 2:
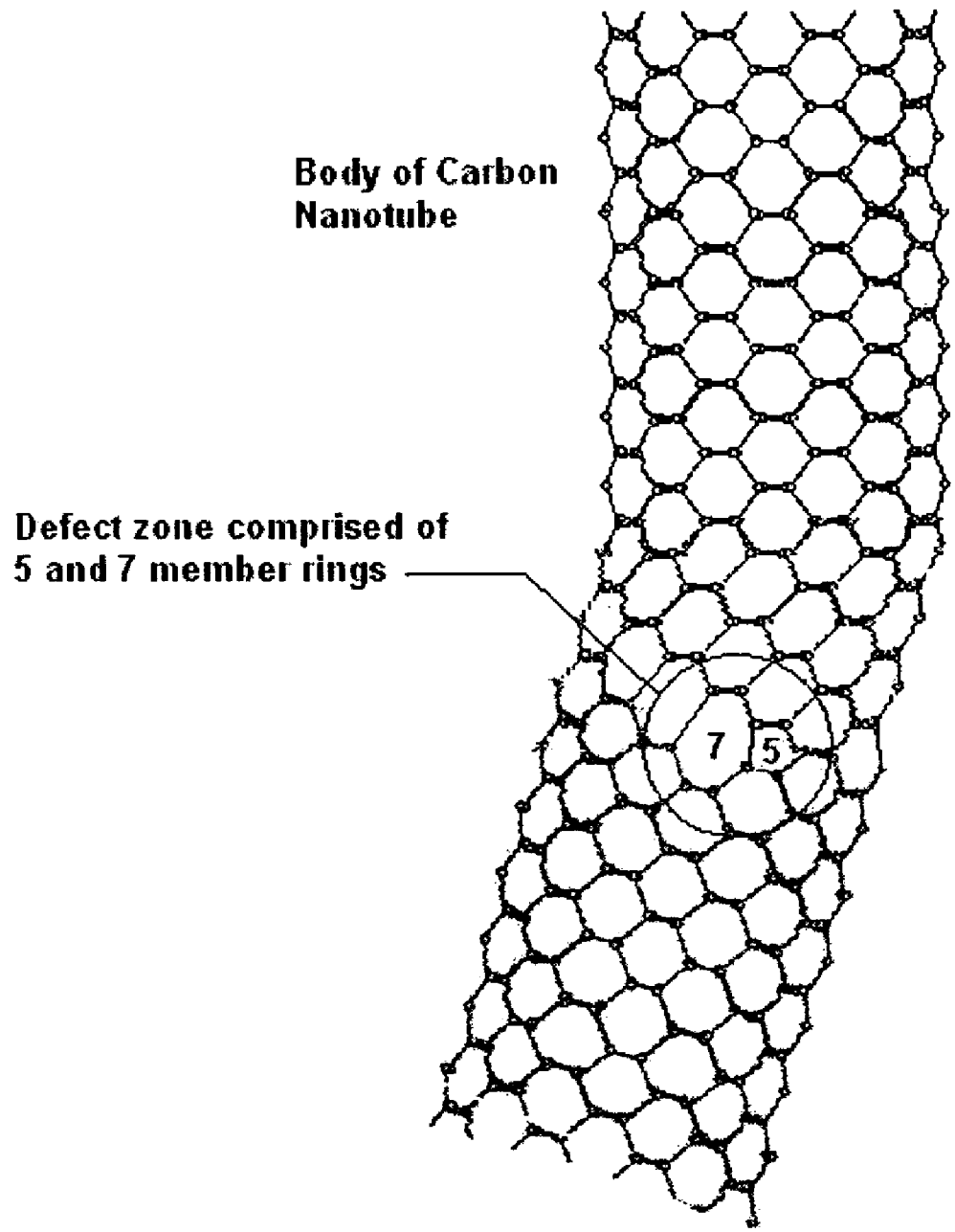
FIG. 2 represents a lattice distortion in a defective carbon nanotube.

A "lattice distortion" means any distortion of the crystal lattice of carbon nanotube atoms forming the tubular sheet structure. As exemplified in FIG. 2, a lattice distortion may include any displacements of atoms because of inelastic deformation, or presence of 5 and/or 7 member carbon rings, or a chemical interaction followed by change in $sp^2$ hybridization of carbon atom bonds. Such defects or distortions may lead to a natural bend in the carbon nanotube.

The phrase "exhibit a greater purification performance" means that the nanomesh demonstrates either improvements to the structural integrity of the resultant material, its porosity, its porosity distribution, its electrical conductance, its resistance to fluid flow, geometric constraints, or any combination thereof that lead to an enhancement of contaminant removal. For example, greater purification performance could be due to improved and more efficient adsorption or absorption properties of the individual carbon nanotubes. Further, the more defects there are in the carbon nanotubes, the more sites exist for attaching chemical functional groups. In one embodiment, increasing the number of functional groups present in the nanomesh should improve the performance of the resulting article.

Treatment of Carbon Nanotubes

In the present disclosure, the carbon nanotubes may also undergo chemical and/or physical treatments to alter their chemical and/or physical behavior. These treatments are typically done to enable the resulting article to exhibit a greater purification performance, in the sense defined above.

In one embodiment, the carbon nanotubes may be chemically or physically treated to achieve at least one of the following effects: remove contaminants, add defects, or attach functional groups to defect sites and/or nanotube surface.

Herein, "chemical or physical treatment" means treating with an acid, solvent or an oxidizer for a time sufficient to remove unwanted constituents, such as amorphous carbon, oxides or trace amounts of by-products resulting from the carbon nanotube fabrication process.

An example of the second type of chemical treatment is to expose the carbon nanotubes to an oxidizer for a time sufficient to create defect density on the surface of the carbon nanotube.

An example of the third type of the chemical treatment to attach specific functional groups that have a desired zeta potential (as defined in Johnson, P. R., *Fundamentals of Fluid Filtration*, 2nd Edition, 1998, Tall Oaks Publishing Inc., which is incorporated herein by reference). This will act to tune the zeta potential or the isoelectric point (pH where the zeta potential is zero) of the carbon nanotubes sufficiently to remove a specific set of desired contaminants from a particular fluid.

In another embodiment, the carbon nanotubes comprise atoms, ions, molecules or clusters attached thereto or located therein in an amount effective to assist in the removal and/or modification of contaminants from the fluid.

The carbon nanotubes described herein may also be treated to alter their properties, as well as the contaminants that may be removed from and/or modified within the fluid. For example, in one embodiment, the carbon nanotubes are chemically treated with an oxidizer, chosen from but not limited to a gas containing oxygen, nitric acid, sulfuric acid, hydrogen peroxide, potassium permanganate, and combinations thereof. Nanotubes which have been treated with an oxidizer can provide unique properties, either in terms of fluid flow, dispersion of nanotubes in the deposition fluid, or from a functionalization perspective (e.g., having the ability to be particularly functionalized).

Figure 3:
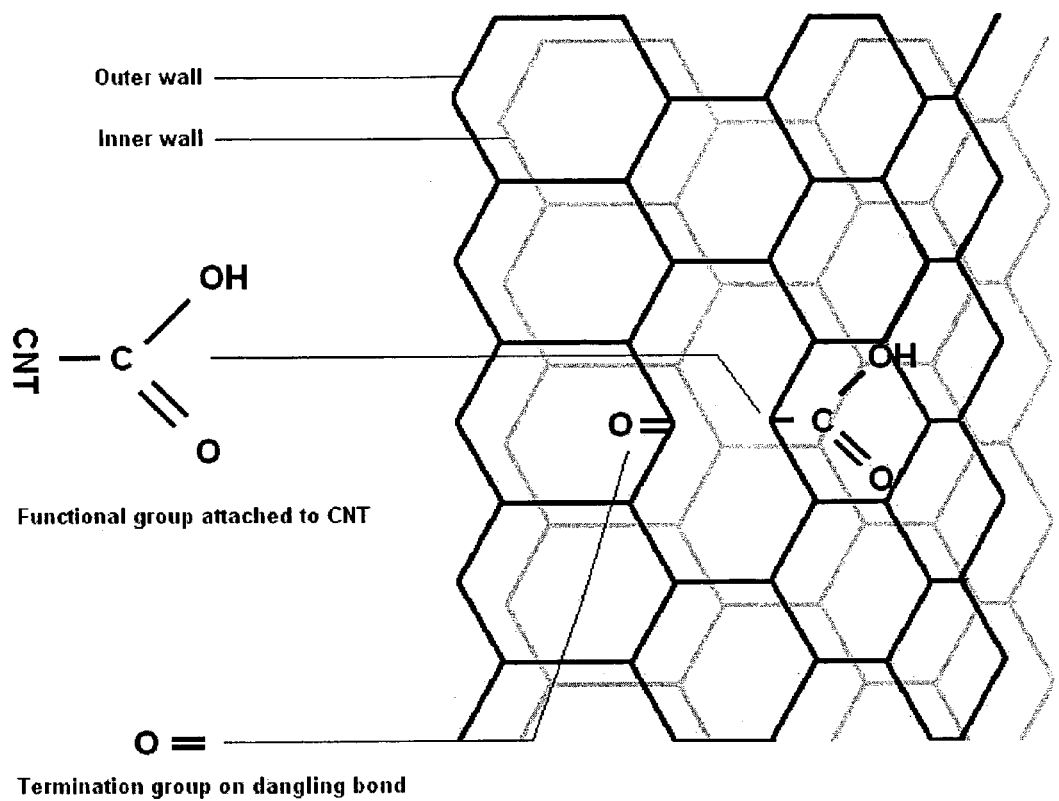
FIG. 3 represents a section of a carbon nanotube functionalized with a carboxyl functional group.

As used herein, "functionalized" (or any version thereof) refers to a carbon nanotube having an atom or group of atoms attached to the surface that may alter the properties of the nanotube, such as zeta potential. Functionalization is generally performed by modifying the surface of carbon nanotubes using chemical techniques, including wet chemistry or vapor, gas or plasma chemistry, and microwave assisted chemical techniques, and utilizing surface chemistry to bond materials to the surface of the carbon nanotubes. These methods are used to "activate" the carbon nanotube, which is defined as breaking at least one C—C or C-heteroatom bond, thereby providing a surface for attaching a molecule or cluster thereto. As shown in FIG. 3, functionalized carbon nanotubes comprise chemical groups, such as carboxyl groups, attached to the surface, such as the outer sidewalls, of the carbon nanotube. Further, the nanotube functionalization can occur through a multi-step procedure where functional groups are sequentially added to the nanotube to arrive at a specific, desired functionalized nanotube.

The functionalized carbon nanotubes can comprise a non-uniform composition and/or density of functional groups including the type or species of functional groups across the surface of the carbon nanotubes. Similarly, the functionalized carbon nanotubes can comprise a substantially uniform gradient of functional groups across the surface of the carbon nanotubes. For example, there may exist, either down the length of one nanotube or within a collection of nanotubes, many different functional group types (i.e. hydroxyl, carboxyl, amide, amine, poly-amine and/or other chemical functional groups) and/or functionalization densities.

Further, other components of the nanomesh, such as fibers and/or nanoparticles, may also be functionalized with chemical groups, decorations or coatings or combinations thereof to change their zeta potential and/or cross-linking abilities and thereby improve the filtration performance of the nanomesh.

A non-limiting example of performing a specific multi-step functionalization is one that allows the zeta potential of carbon nanotubes to be controlled and improve their ability to remove viruses. The carbon nanotubes are refluxed in a mixture of acids. While not being bound by any theory, it is believes that such a process increase the number of defects on the surface of the nanotube, increasing carboxyl functional groups attached to the defect locations, and/or changes the zeta potential of the nanotubes due to the negative charge of carboxyl functional groups in water.

Carboxyl functionalized nanotubes may then refluxed in a solution of thionyl chloride in a nitrogen atmosphere. Without being held to any theory, it is believes that this acts to convert the previously attached carboxyl functional groups to acyl chloride functional groups. Subsequently, these acyl chloride functionalized nanotubes are refluxed in as solution of ethylenediamine again in a nitrogen atmosphere. It is believed that this reacts with the amine groups on the end of the diamine with the acyl chloride functional group, thereby converting the acyl chloride functional group to a 2-aminoethylamide functional group by replacement of the chlorine atom with one amine group of the diamine. The termination of the nanotube functionalization with an amine group, will impart a positive charge to the nanotube in water, giving it a positive or less negative zeta potential. The foregoing would enable a nanomesh device constructed with nanotubes of this type to specifically target negatively charged contaminants (such as anions, certain molecules, and virus particles) for capture by Van der Waals and/or electrostatic forces, leading to their removal from the contaminant stream.

In another embodiment, carbon nanotubes can also be used for high surface area molecular scaffolding either for functional groups comprised of organic and/or inorganic receptors or to provide structure and support for natural or bioengineered cells [including bacteria, nanobacteria and extremophilic bacteria]. Examples of nanobacteria, including images of nanobacteria in carbonate sediments and rocks can be found in the following references, which are herein incorporated by reference. R. L. Folk, *J. Sediment. Petrol.* 63:990-999 (1993), R. H. Sillitoe, R. L. Folk and N. Saric, *Science* 272: 1153-1155 (1996). The organic and/or inorganic receptors will selectively target the removal of specific contaminants from a fluid stream. The natural or bioengineered cells supported by the nanotubes will consume, metabolize, neutralize, and/or bio-mineralize specific biologically-active contaminants. For example, there are specific microorganisms adhered to the nanotubes that can reduce the toxicity of oil spills.

In another aspect of this invention, the carbon nanotubes, the carbon nanotube material, or any subassembly thereof may be treated with radiation. The radiation may be chosen from but not limited to exposure from electromagnetic radiation and/or at least one particle chosen from electrons, radionuclides, ions, particles, clusters, molecules or any combination thereof. As previously described, the radiation should impinge upon the carbon nanotube in an amount sufficient to 1) break at least one carbon-carbon or carbon-heteroatom bond; 2) perform cross-linking between nanotube-nanotube, nanotube to other nanomesh constituent, or nanotube to substrate; 3) perform particle implantation, 4) improve the chemical treatment of the carbon nanotubes, or any combination thereof. Irradiation can lead to a differential dosage of the nanotubes (for example due to differential penetration of the radiation) which causes non-uniform defect structure within the nanomesh structure. This may be used to provide a variation of properties, via a variation of functional groups attached to the carbon nanotubes.

Figure 4:
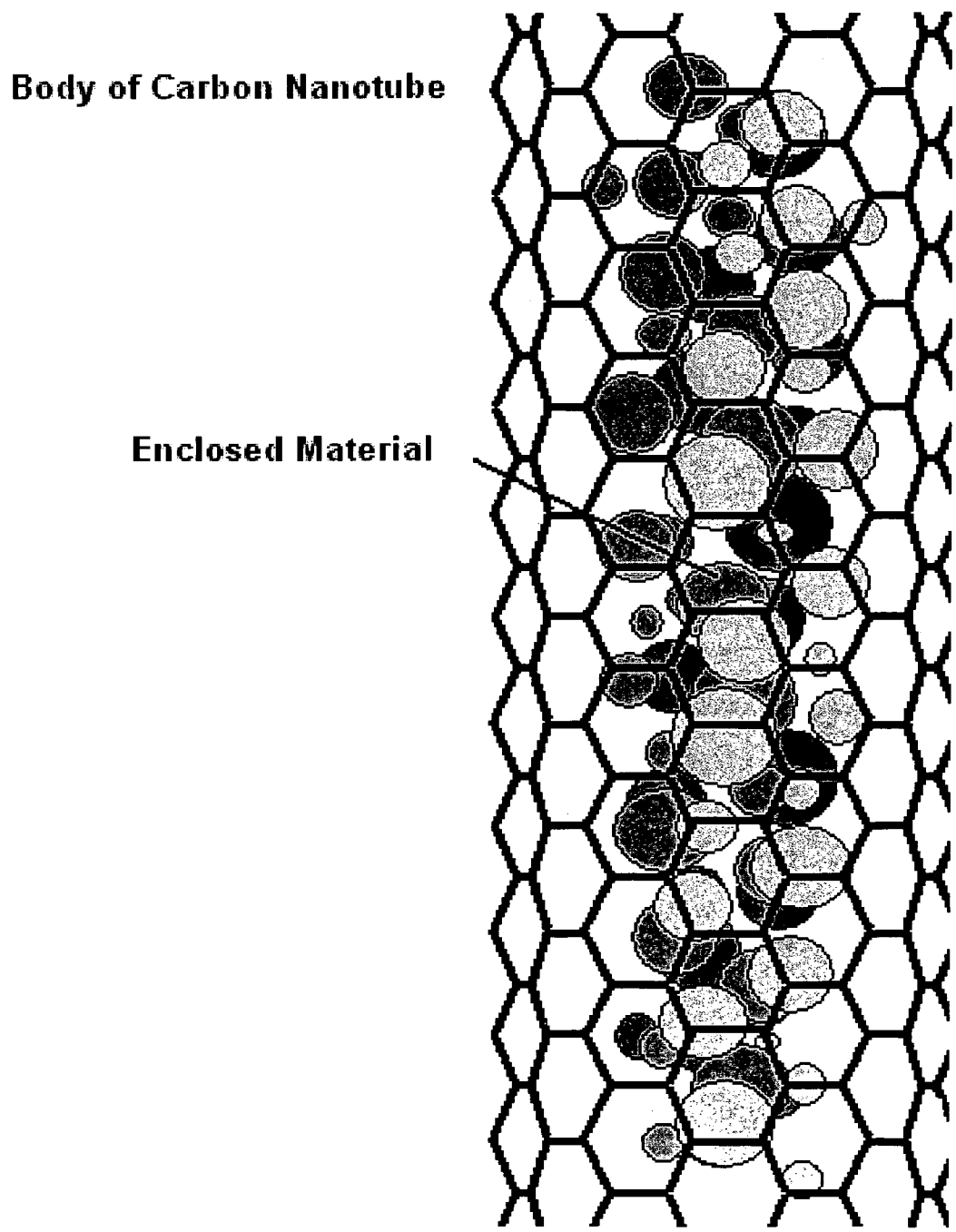
FIG. 4 represents a filled carbon nanotube.

The carbon nanotubes described herein may also be filled or impregnated with a desired material to achieve certain beneficial properties. The terms "filled" or "impregnated" can be used interchangeably, and refer to carbon nanotubes that are at least partially filled with a substance of interest. The substance filled or impregnated into the carbon nanotube can typically improve the nanomesh filtration performance and/or specifically re-target its application. A non-limiting example is the improvement of filtration through increased nanotube affinity for specific contaminants. For example, if an article is to be used to remove an electronegative contaminant, such as arsenic complexes in water, the carbon nanotubes are first impregnated with an electropositive substance. FIG. 4 exemplifies a carbon nanotube that is filled with a substance.

In addition, carbon nanotubes, according to the present disclosure, may be modified by coating or decorating with a material and/or one or many particles to assist in the removal of contaminants from fluids or increase other performance characteristics such as mechanical strength, bulk conductivity, or nano-mechanical characteristics. Unlike functionalized carbon nanotubes, coated or decorated carbon nanotubes are covered with a layer of material and/or one or many particles which, unlike a functional group, is not necessarily chemically bonded to the nanotube, and which covers a surface area of the nanotube sufficient to improve the filtration performance of the nanomesh.

Figure 5:
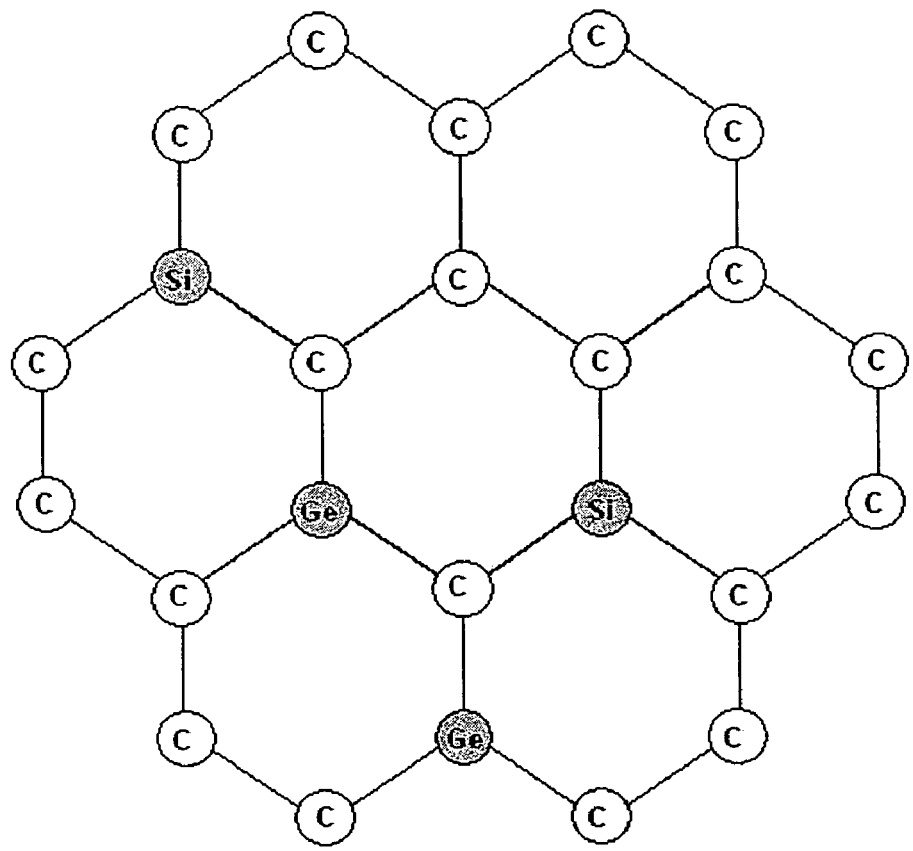
FIG. 5 represents a section of a carbon nanotube doped with different atoms.

Carbon nanotubes used in the article described herein may also be doped with constituents to assist in the removal of contaminants from fluids. As used herein, a "doped" carbon nanotube refers to the presence of ions or atoms, other than carbon, into the crystal structure of the rolled sheets of hexagonal carbon. As exemplified in FIG. 5, doped carbon nanotubes means at least one carbon in the hexagonal ring is replaced with a non-carbon atom.

In another embodiment, carbon nanotubes as described herein could be decorated by a cluster or clusters of atoms or molecules. As used herein "decorated" refers to a partially coated carbon nanotube. A "cluster" means at least two atoms or molecules attached by any chemical or physical bonding.

The clusters can exhibit properties of quantum dots resulting in photo-stable, color-tunable, nanocrystal with a wide absorption spectrum and a narrow emission peak. Clusters, including quantum dots, may be comprised of metals, non-metals and combinations thereof. These attached clusters may be subsequently photo-activated to remove, disable and/or destroy contaminants. A quantum dot is a particle of matter so small that the addition or removal of an electron can be detected, and changes its properties in some useful way. In one embodiment, a quantum dot is a semiconductor crystal with a diameter of a few nanometers, also called a nanocrystal, that because of its small size behaves like a potential well that confines electrons in three dimensions to a region of a few nanometers.

The molecules or may include inorganic compounds containing at least one metal atom chosen from: lithium, sodium, magnesium, aluminum, potassium, calcium, scandium, titanium, vanadium, chromium, manganese, iron, cobalt, nickel, copper, zinc, gallium, rubidium, strontium, yttrium, zirconium, niobium, molybdenum, rhodium, palladium, silver, indium, tin, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, bismuth and at least one nonmetal atom chosen from: hydrogen, boron, carbon, nitrogen, oxygen, fluorine, silicon, phosphorus, sulfur, chlorine, bromine, antimony, iodine and combinations thereof.

The molecules or clusters may also include organic compounds containing at least one protein, including natural polymers composed of amino acids joined by peptide bonds, carbohydrates, polymers, aromatic or aliphatic alcohols, and nucleic or non-nucleic acids, such as RNA and DNA.

Non-limiting examples of the organic compound may comprise at least one chemical group chosen from carboxyls, amines, arenes, nitriles, amides, alkanes, alkenes, alkynes, alcohols, ethers, esters, aldehydes, ketones, polyamides, polyamphiphiles, diazonium salts, metal salts, pyrenyls, thiols, thioethers, sulfhydryls, silanes, and combinations thereof.

The foregoing list of polymeric, ceramic, metallic, and biological materials encompasses the same materials that may fill, functionalize, or coat the carbon nanotubes. It has been discovered that such materials can be attached to or placed within the carbon nanotubes more easily if the surface of the carbon nanotubes is purposely defected.

Fibers Included in the Nanomesh

The nanomesh described herein may also comprise fibers which act to maintain the dispersion (or exfoliation) of the carbon nanotubes during processing. Such fibers can be sacrificial (removed from the structure during further processing, such as by chemical or heat treatments) or can remain an integral part of the finished device. Typically these fibers have a diameter ranging from 1 nm to 1 mm, such as from 10 nm to 100 μm.

As used herein, the term "fiber" means an object of length L and diameter D such that L is greater than D, wherein D is the diameter of the circle in which the cross section of the fiber is inscribed. For example, the aspect ratio L/D (or shape factor) is chosen ranging, for example, from 2 to $10^9$, such as from 5 to $10^7$ and further such as from 5 to $10^6$.

The fibers that may be used in the composition disclosed herein may be mineral or organic fibers of synthetic or natural origin. They may be short or long, individual or organized, for example, braided, and hollow or solid. They may have any shape, and may, for example, have a circular or polygonal (square, hexagonal or octagonal) cross section, depending on the intended specific application.

The fibers have a length ranging, for example, from 10 nm to 10 m, such as from 20 nm to 1 cm. Their cross section may be within a circle of diameter ranging, for example, from 1 nm to 1 mm.

The fibers can be those used in the manufacture of textiles as derived from bio-mineralization or bio-polymerization, such as silk fiber, cotton fiber, wool fiber, flax fiber, feather fibers, cellulose fiber extracted, for example, from wood, legumes or algae.

Medical fibers may also be used in the present disclosure. For instance, the resorbable synthetic fibers may include: those prepared from glycolic acid and caprolactone; resorbable synthetic fibers of the type which is a copolymer of lactic acid and of glycolic acid; and polyterephthalic ester fibers. Nonresorbable fibers such as stainless steel threads may be used.

The fibers may be chosen from:

(a) at least one polymeric material chosen from single or multi-component polymers such as nylon, acrylic, methacrylic, epoxy, silicone rubbers, synthetic rubbers, polypropylene, polyethylene, polyurethane, polystyrene, polycarbonates, aramids (i.e. Kevlar® and Nomex®), polychloroprene, polybutylene terephthalate, poly-paraphylene terephtalamide, poly (p-phenylene terephtalamide), and polyester ester ketone, polyesters [e.g. poly(ethylene terephthalate), such as Dacrone®], polytetrafluoroethylene (i.e. Teflon®), polyvinylchloride, polyvinyl acetate, viton fluoroelastomer, polymethyl methacrylate (i.e. Plexiglass®), and polyacrylonitrile (i.e. Orlon®), and combinations thereof;

(b) at least one ceramic material chosen from boron carbide, boron nitride, spinel, garnet, lanthanum fluoride, calcium fluoride, silicon carbide, carbon and its allotropes, silicon oxide, glass, quartz, silicon nitride, alumina, aluminum nitride, aluminum hydroxide, hafnium boride, thorium oxide, cordierite, mullite, ferrite, sapphire, steatite, titanium carbide, titanium nitride, titanium boride, zirconium carbide, zirconium boride, zirconium nitride, and combinations thereof;

(c) at least one metallic material chosen from aluminum, boron, copper, cobalt, gold, platinum, palladium, silicon, steel, titanium, rhodium, iridium, indium, iron, gallium, germanium, tin, tungsten, niobium, magnesium, manganese, molybdenum, nickel, silver, zirconium, yttrium, their oxides, hydrides, hydroxides and alloys thereof;

(d) at least one biological material or derivative thereof chosen from cotton, cellulose, wool, silk, and feathers, and combinations thereof; and (e) at least one carbon nanotube chosen from single walled, double walled or multi-walled carbon nanotubes that have either a nested or non-nested morphology of nano-horns, nano-spirals, nano-springs, dendrites, trees, spider nanotube structures, nanotube Y-junctions, and bamboo morphology or multi-stranded helices;

(f) at least one metallic oxide or metallic hydroxide nanowire. For example, a metal oxide nanowire can be prepared by heating metal wires with oxygen in a reaction vessel to a temperature ranging from 230-1000° C. for a period ranging from 30 minutes to 2 hours. The nanowires will grow by using macroscale wires made any metal previously mentioned as a feedstock. The resulting metallic oxide nanowires can be in a size ranging from 1-100 nanometers in diameter, such as 1-50 nanometers in diameter, including 2-5 nanometers in diameter. In one advantageous aspect of this process, the surface of the base wire is abraded to provide a roughened surface texture to enable better nanotube adhesion within the nanomesh as well as enhance the purification performance of the article. These metal oxide or metal hydroxide nanowires can also be obtained from commercial suppliers.

Substrates Used in the Device

In one embodiment, the article includes a porous support substrate for depositing the carbon nanotubes using a differential pressure process. The porous support substrate may be in any form suitable for the shape of the resulting article, such as a block, tube (or cylinder), sheet or roll, and may comprise a material chosen from ceramic, carbon, metal, metal alloys, or plastic or combinations thereof. In one embodiment, the substrate comprises a woven or non-woven fibrous material.

Figure 6:
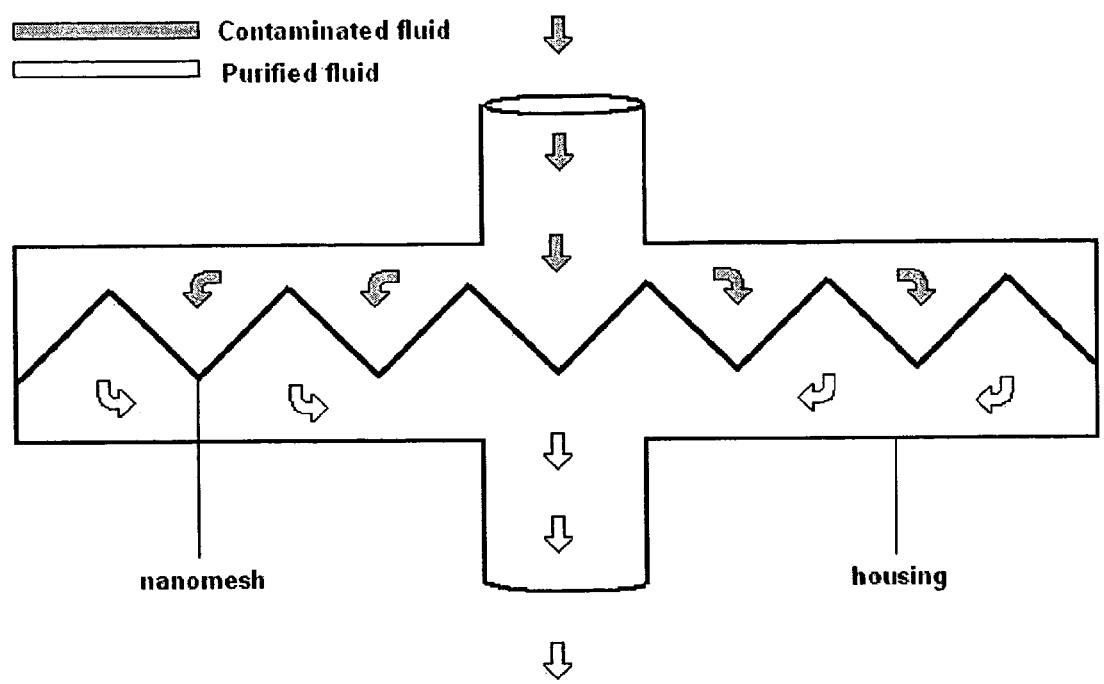
FIG. 6 represents a fluid purification device comprising carbon nanotubes wherein the substrate possesses a pleated design.

Further, when the substrate takes the form of sheet, the substrate may be either a flat or planar sheet or in a pleated form (FIG. 6). The pleated form being chosen to increase the surface area of the nanomesh exposed to contaminated fluid.

In one embodiment, the substrate is a roll of material on which the nanomesh is deposited. In this process, the roll may be scrolled through a series of deposition and other processing stations in either a continuous or semi-continuous manner.

Figure 7:
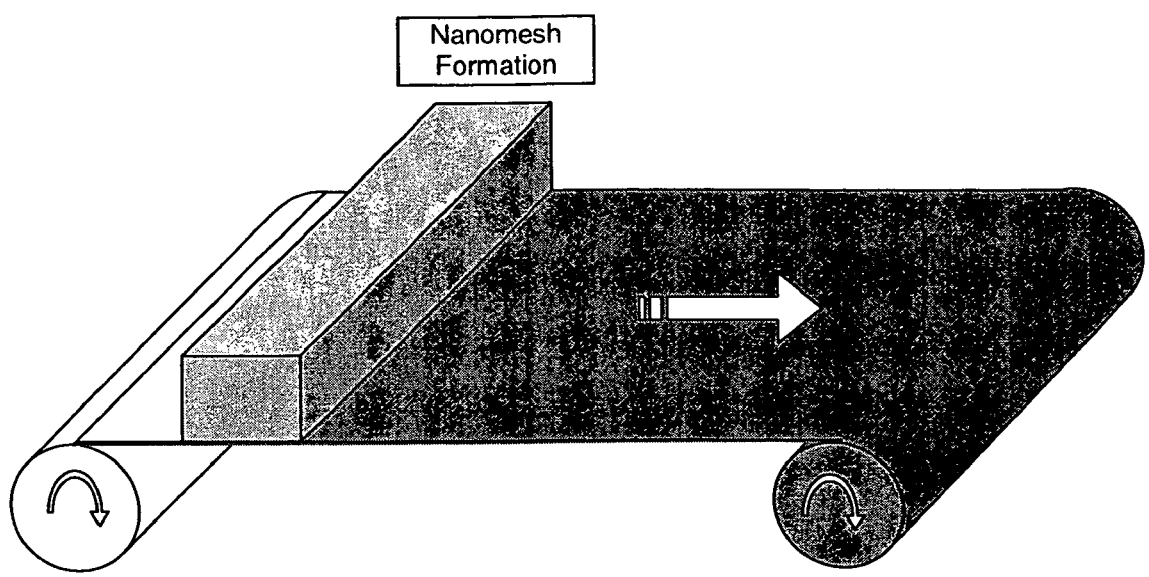
FIG. 7 represents a method of depositing carbon nanotubes on a rolled substrate that may be wrapped around a cylinder, block or other bulk material.

In another embodiment, wherein the nanomesh is created by a rolled process, it may be used to wrap around a hollow, porous cylinder, block or other supporting structure to form the filter media as depicted in FIG. 7.

In another embodiment, the porous tubular substrate comprises a carbon material, such as activated carbon (bulk or fiber), the outer surface of which is coated with the carbon nanotubes described herein.

In another embodiment, a collection of metal oxide/hydroxide nanowires, made as described above, may also be used as a substrate for the deposition(s) of carbon nanotubes using a differential pressure deposition process. The resulting nano-wire/carbon nanotube nanomesh may or may not be treated thermally, mechanically, or chemically to enhance structural integrity and/or improve the purification performance of the article. The chemical treatments may include the functionalizing, coating or decoration of the resultant nanomesh with chemical groups, metals, ceramics, plastics, or polymers. Further these chemical treatments may be done so that they the nanomesh article chemically or physically reacts or interacts with contaminants to destroy, modify, immobilize, remove, or separate them.

In other embodiments, the porous support substrate used during the differential pressure deposition process may be either sacrificial or used only temporarily during deposition to form the nanomesh in a method analogous to paper manufacturing.

Other Manifestations of the Device

Another embodiment of the article comprises multiple nanomesh layers, each of which may be specifically, and independently, tuned through its zeta potential or other means to remove a specific distribution of contaminants or to improve other performance characteristics of the article. The phrase, "other means" is intended to mean the tuning of specific properties of the nanomesh layer such as its porosity, the contaminant affinity [e.g. functionalization of nanomesh components, specific contaminant(s) receptors], or strength (e.g. binding or cross-linking agents used).

In another embodiment, the nanomesh contains a binding agent (such as polyvinyl alcohol) that acts to improve the filtration performance of the article. Such a binding agent may be introduced into the suspension containing the carbon nanotubes and other nanomesh components prior to the formation of the nanomesh structure.

In another embodiment, the nanomesh can be formed through a process of self assembly. "Self assembly" means that the nanomesh components arrange themselves into the final nanomesh structure. This is accomplished by controlling the electric, magnetic, chemical and geometric constraints through the choice of functional groups, surface charge distributions, the composition or properties of the dispersive agent, or any combination thereof. For example, adjusting the surface charge distribution of the nanomesh components controls their electrical behavior, which in turn determines how they arrange into the structure of the assembled nanomesh. This self assembly may be in any form that leads to an enhanced structural framework within the nanomesh that improves the removal properties, porosity, electrical resistance, resistance to fluid flow, strength characteristics or combinations thereof.

Further, the above self assembly may be "directed" through the imposition of an external field. This applied field works in concert with the properties of any or all of the nanomesh components and/or the fluid in which the components are suspended to guide their assembly into the resulting nanomesh. For example, a suspension containing some or all of the components of the nanomesh may be subjected to electromagnetic stimulation during the formation of the nanomesh to achieve a desired component alignment and/or weaving to enhance the fluid purification performance.

Mechanisms of Action

Fluid Sterilization

Without wishing to be bound by any theory, it is believed the nanomesh described herein forms a unique nanoscopic interaction zone that uses chemical and physical forces to first attract then to modify or separate microbes and other pathogens from the fluid stream. For example, it is believed that during the sterilization of a fluid, microorganisms come into contact with the nanomesh, causing focused forces to be applied to the microorganisms. These forces first attract, then either cause adherence and/or modification of cells. It is possible that this modification involves disrupting the cell membranes or causing internal cellular damage, thus disabling and/or destroying the microorganisms or their ability to reproduce. In this way, fluids can be effectively sterilized with respect to microorganisms. Common microorganisms are in the size range of 1-5 microns long and as such are at least 100 times larger than a nanostructure such as carbon nanotubes. Known examples of these organisms include *E. coli, Vibrio cholera, Salmonella typhi, Shigella dysenteriae, Cryptosporidium parvum, Giardia lamblia, Entamoeba histolytica*, and many others. Examples of viruses transmitted through water include *Polio, Hepatitis A, Rotavirus, Enteroviruses* and many others. Examples of chemical agents include, but are not limited to, ions, heavy metals, pesticides, herbicides, organic and inorganic toxins, and microbial toxins (such as that causing botulism).

Due to the large size differences, forces on the nanoscopic scale can be applied that are orders of magnitude more intense than those based on micro- or macroscopic technologies. By analogy to the way that focused light gives the intensity to a laser, focused forces give the intensity to nanoscale attraction and/or destruction of microbes. Thus, mechanical and electrical forces that are on larger scales either too small to be effective or very energy-intensive, on the nanoscale can be used to effectively and efficiently remove or destroy microorganisms.

Mechanisms believed to be capable of adsorbing then destroying microorganisms in this nano-regime can act independently or in concert with one another. Non-limiting examples of such mechanisms include:

- Mechanical penetration and/or abrasion of the cell wall through focused forces;
- Vibrational waves causing either external damage to the cell wall and transport channels and/or internal cellular damage to the DNA, RNA, proteins, organelles, etc.;
- Bubble cavitations from shockwaves in the liquid around the carbon nanotubes which damage the cell structure;
- Electromagnetic, electrostatic and/or Van der Waals forces which capture and hold biological contaminants;
- Disruption of hydrogen bonding in the vicinity of nanostructures via zeta action causing damage to cell walls and/or DNA;
- Acidification of the environment around the nanostructure, due to specific nanotube functionalizations that attract naturally occurring $H^+$ ions in water, which damages cell walls and/or DNA.

Since the osmotic pressure within a typical microbial cell is higher than that of the surrounding fluid, assuming non-physiological conditions, even slight damage to the cell wall can cause total rupture as the contents of the cell flow from high to low pressure. Further, sufficient damage to the DNA of a viral or microbial cell can destroy at least one microorganism's ability to reproduce or infect host cells rendering it incapable of causing infection.

Nano-electronic Fluid Purification

According to the present disclosure, another process of fluid purification is also based on the nanomesh article. In this case, an electrostatic or electromagnetic field is imposed upon a nanomesh to control the purification of a fluid. Much like the behavior of electro-static separation devices, the imposition of an electric potential across the nanomesh can remove contaminants on the nanoscale. Further, this process can be used in reverse to cleanse the filter article.

In addition, the entire nanomesh can be stimulated with dynamic electromagnetic fields which, when properly adjusted, will excite nanomesh-wide vibrations. These vibrations could have both microorganism damaging effects or induce an ultrasonic self-cleaning effect. The utility of the inventive article, in this connection, is that advantage is taken of the high strength, high stiffness (large Young's modulus), high conductivity, and the piezo-electric property of the nanotubes.

Figure 8:
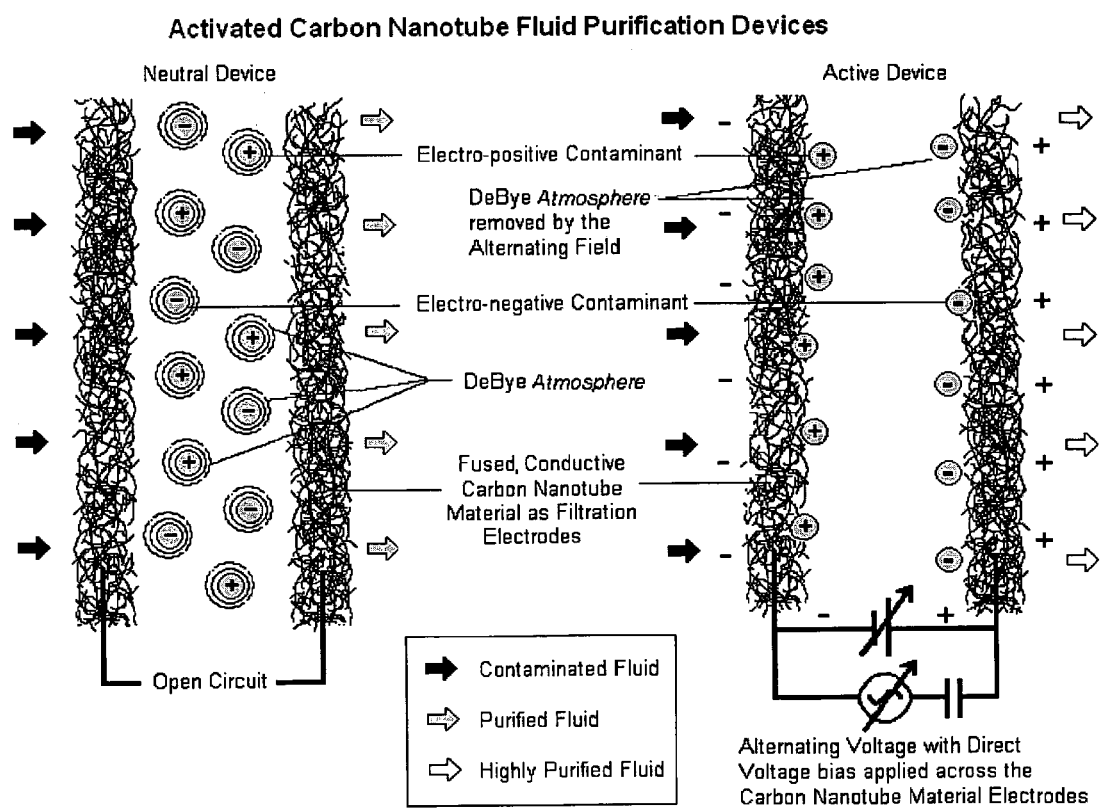
FIG. 8 schematically represents the desalination device showing electrical connection to the nanomesh layers.

Additionally, for some applications, the imposition of a more generalized electromagnetic field can give fluid purification performance that goes beyond existing technologies. For example, in the case of two conducting nanomesh layers, imposing an electric current generates a magnetic field between nanomesh layers (FIG. 8). This field could be tuned to capture all charged particles from a fluid stream.

Liquid Desalination

According to the present disclosure, a process of liquid desalination is also based on the described nanomesh article. One mechanism believed to be capable of desalinating liquid with the described nanomesh, is the imposition of a voltage differential between two or more nanomesh membranes. In this case, one nanomesh membrane carries a positive charge and the other membrane a negative charge. The applied potential causes cations to migrate toward the negatively charged membrane and anions to migrate toward the positively charged one. Due to the large surface area ($1000 \, m^2/gram$) of carbon nanotubes, the application a voltage differential across the nanomesh membrane creates a very high capacitance device, thereby creating a efficient, compact, reversible ionic separation zone (i.e. an ion trap).

Figure 9:
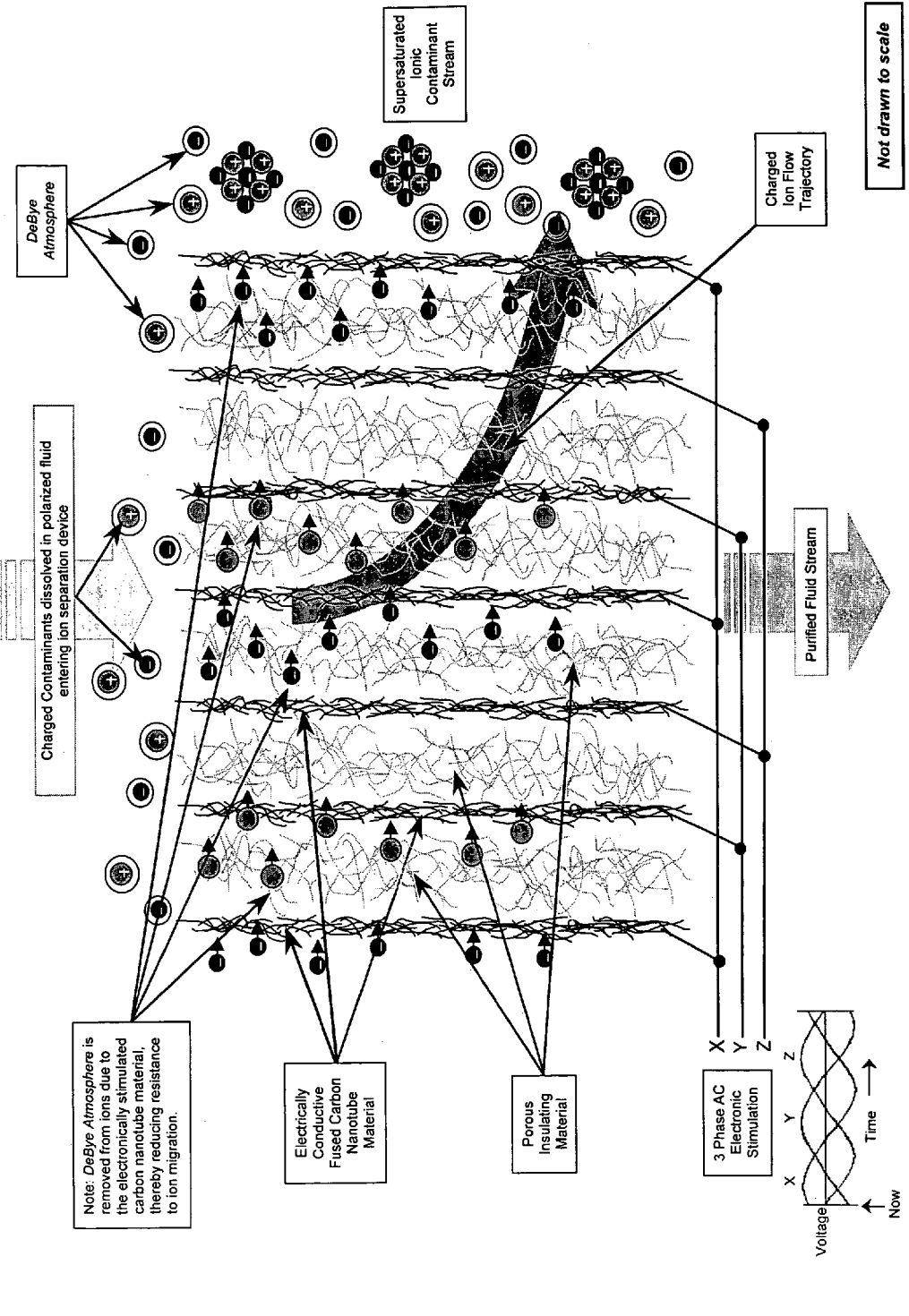
FIG. 9 represents the dynamics of ion motion through a sequence of nanomesh membranes in active mode using both a low-frequency, three-phase AC signal (to drive ion motion)

A desalination unit could incorporate two or more parallel layers of supported conductive nanomesh that are electrically isolated from each other. The two or more layers may be electrically charged in either a static or active mode. In static mode, for example, the nanomesh layers could be oppositely charged to create a salt trap between them. In an active mode device with four or more layers, for example, a four phase signal would be applied to the multi-layer nanomesh structures such that the four legs of the signal are applied to four sequential nanomesh layers. This pattern is repeated every fourth nanomesh layer (FIG. 9). In this way, the charge on each nanomesh layer and across the device indexes sequentially in time from positive to neutral to negative to neutral. Done sequentially in time would create, electronically, a moving virtual capacitor within the device which can cause the salt ions to migrate in a direction different than the flow of the water through the device. The concentrated salt water would accumulate at the terminus of the virtual capacitor and could be channeled out of a brine port on the device, while the fresh water would pass through the device.

In practice, due to the polarized nature of the water molecule, ions in a water solution have their charges shielded by a cloud of water molecules that surround them, which is described as the DeBye atmosphere in FIG. 10. Because this cloud of water molecules is carried along with the ions as they move, it acts to increase the ions effective mass and ionic radius. Therefore, a higher frequency (relative to the frequency required to induce ion separation) AC signal can be imposed across the membrane layers in the desalination device. The purpose of this higher frequency signal is to disrupt the DeBye atmosphere shielding the ions in solution. As a result of shedding this water molecule shell, the ions appear smaller and less massive and can move with less resistance through the fluid. This aspect of the invention improves the efficiency of the desalination device.

Additionally, the desalination device described herein could be designed to take advantage of the biological removal characteristics of the nanomesh structure, as discussed above, to purify the resulting fresh water.

Prevention of Bio-films

According to one aspect of the present disclosure, surfaces susceptible to bio-film formation, due to the attachment and growth of contaminating microbes, can be coated with a layer of nanomaterial to prevent either the attachment or subsequent growth of undesirable elements, such as molds, bacteria. Non-limiting examples of such nanomaterials include elements or compounds having antibacterial properties (such as iodine resin, silver, aluminum oxide, aluminum hydroxide, or triclosan) that are attached to the surface or located within the carbon nanotube or attached to any other nanomesh component.

Types of Contaminants Removable by the Invention

Non-limiting examples of contaminants that can be removed from fluid using the disclosed article include, but are not limited to, the following biological agents: pathogenic microorganisms [such as viruses (e.g. smallpox and hepatitis), bacteria (e.g. anthrax, typhus, cholera), oocysts, spores (both natural and weaponized), molds, fungi, coliforms, and intestinal parasites], biological molecules (e.g. DNA, RNA), and other pathogens [such as prions and nanobacteria (both natural and synthetic)].

"Prions" are defined as small infectious, proteinaceous particles which resist inactivation by procedures that modify nucleic acids and most other proteins. Both humans and animals are susceptible to prion diseases [such as Bovine Spongiform Encephalopathy (BSE or Mad Cow disease) in cows, or Creutzfeld-Jacob Disease (CJD) in humans].

"Nanobacteria" are nanoscale bacteria, some of which have recently been postulated to cause biomineralization in both humans and animals. It has further been postulated that nanobacteria may play a role in the formation of kidney stones, some forms of heart disease and Alzheimer's Disease. Further, nanobacteria are also suspected of causing unwanted biomineralization and/or chemical reactions in some industrial processes.

Other non-limiting examples of contaminants that can be removed from fluid using the disclosed article include, but are not limited to noxious, hazardous or carcinogenic chemicals comprised of natural and synthetic organic molecules (such as toxins, endotoxins, proteins, enzymes, pesticides, and herbicides), inorganic contaminants (such as heavy metals, fertilizers, inorganic poisons) and ions (such as salt in seawater or charged airborne particles).

Applications of the cleaned fluid, specifically clean water, include potable water, irrigation, medical and industrial. For example, as a source of de-ionized water for industrial processes including, but not limited to, semiconductor manufacturing, metal plating, and general chemical industry and laboratory uses.

More specifically, the chemical compounds that may be removed from fluid using the article described herein are removal target atoms or molecules that include at least one atom or ion chosen from the following elements: antimony, arsenic, aluminum, selenium, hydrogen, lithium, boron, carbon, oxygen, calcium, magnesium, sulfur, chlorine, niobium, scandium, titanium, vanadium, chromium, manganese, iron, cobalt, nickel, copper, zinc, gallium, germanium, bromine, strontium, zirconium, yttrium, molybdenum, rhodium, palladium, iodine, silver, cadmium, indium, cesium, tin, barium, lanthanum, tantalum, beryllium, copper, fluoride, mercury, tungsten, iridium, hafnium, rhenium, osmium, platinum, gold, mercury, thallium, lead, bismuth, polonium, radon, radium, thorium, uranium, plutonium, radon and combinations thereof.

Generalized Construction of the Invention

Another aspect of the present disclosure relates to a method of making a nanomesh material to be used in an article for removing contaminants from fluid, such as a nanomesh material comprises functionalized carbon nanotubes. The general process for making a nanomesh comprising functionalized carbon nanotubes and treated glass fibers eventually used in a cylindrical article is described in FIG. 11. It is noted, however, that the following process can be used to describe the fabrication of any shape article wherein carbon nanotubes are mixed, or not, with an additional substance prior to deposition. For example, in the following schematic representation of the process, the "Treated Glass Fiber" described in step 2 would simply be replaced with another substance chosen from any described herein and the substrate described in step 4 would simply change from "cylindrical carbon block" to any desired material and shape, such as a flat woven substrate, when used in an air purification device.

Examples of the resulting device comprising the previously mentioned nanomesh filters are shown in FIGS. 12 and 13. For example, FIG. 12 is a side perspective of an article comprising a hollow tube of activated carbon having a nanomesh of carbon nanotubes thereon. In this embodiment, the contaminated fluid flows through the outer wall of the tube with the purified fluid exiting the device from the interior of the hollow tube. For example, FIG. 13 is a representation of a flat or planar purification device.

1. Preparation of Functionalized Carbon Nanotubes

One process for preparing functionalized carbon nanotubes generally comprises an initial sonication of commercially available carbon nanotubes in a solvent. Such carbon nanotubes include multi-wall carbon nanotube powder made by any chemical process, such as Chemical Vapor Deposition (CVD) oven process that typically has a purity >95% by weight, and characteristic dimensions of 500 nm-50 µm in length, such as 10-20 µm, and 2-200 nm in diameter.

Therefore, subsequent to, or simultaneous with, sonication the carbon nanotubes are treated in acid, chosen from but not limited to nitric, sulfuric, hydrochloric, and/or hydrofluoric acid or combination thereof. These acids can be used individually to wash the carbon nanotubes, or be used in various combinations. For example, in one embodiment, the carbon nanotubes are first washed in nitric acid and then washed in hydrofluoric acid. In another embodiment, the carbon nanotubes are washed in sulfuric acid after being washed in nitric acid.

The acid wash is performed to remove any contaminants, such as amorphous carbon, or catalyst particles and their supports which may interfere with the surface chemistry of the nanotube, and producing functional groups (such as carboxyl, for example) attached to the defect locations on the surface of the carbon nanotubes.

This functionalization also provides hydrophilicity to the carbon nanotubes, which is thought to improve the filtration performance of the resulting article. The carbon nanotubes are then subjected to a final distilled water rinse, and suspension in an appropriate dispersant, such as distilled water, or an alcohol, such as ethanol or isopropanol. In one embodiment, sonication, stirring and heating is employed throughout this functionalization process to maintain adequate dispersion of the nanotubes while cleaning.

2. Preparation of Metal Oxide Treated Fibers

In one embodiment, the process of making a nanomesh for use in the described article comprises mixing the previously described functionalized carbon nanotubes with metal oxide (such as iron oxide) or metal hydroxide (such as iron hydroxide) treated (either coated or decorated) fibers as disclosed herein. The preparation of such metal oxide or metal hydroxide treated glass fibers may comprise mixing a metal oxide or metal hydroxide containing solution with commercially available glass fibers, such as fibers having a diameter ranging from 0.2 µm-5 µm.

In one embodiment, the process comprises stirring the glass fibers with a mixture of distilled water and colloidal metal oxide or metal hydroxide solution for a time sufficient to treat the glass fibers. The treated fibers may then be dried in an oven.

3. Preparation of Suspensions

The ingredients used to make the suspension comprise the functionalized carbon nanotube solution and the metal oxide or metal hydroxide treated fibers prepared in the previously mentioned processes. To prepare the component parts of the suspension, the functionalized carbon nanotubes are first dispersed in an appropriate medium, such as water or ethanol, by sonication. The metal oxide or hydroxide treated glass fibers are separately dispersed in a container, again in an appropriate medium, such as water or ethanol. These separate dispersions are then mixed to form a suspension of functionalized carbon nanotubes and metal oxide or metal hydroxide treated fibers.

In one embodiment, the structure of the final nanomesh may comprise different layers of functionalized carbon nanotubes and metal oxide or metal hydroxide treated glass fibers. These different layers are formed from distinct suspension made from different ratios of carbon nanotubes and treated glass fiber.

4. Deposition of Carbon Nanomesh

The procedure for depositing the functionalized carbon nanotube/treated fiber mixture including, but not limited to, metal oxide or metal hydroxide coating of any of the fibers disclosed here in. For example, the nanomesh can be made from the carbon nanotube/treated fiber mixture using a differential pressure deposition or direct assembly. In this embodiment, the deposition process uses differential pressure across the substrate to deposit the functionalized carbon nanotube/metal treated fiber suspension onto a carbon block substrate. In this embodiment, the pressure difference applied across the substrate is such that the pressure is lower inside the substrate block. This differential pressure forces the fluid comprising the suspension to flow through the substrate, depositing carbon nanotube/glass fiber mixture on the outer surface of the substrate, thereby forming the nanomesh.

5. Article Assembly

After the nanomesh material is dried, the coated substrate is covered with a porous protective paper and a coarse plastic netting to protect the nanomesh material. End caps are then attached and the edges of the nanomesh sealed to prevent fluid circumventing the nanomesh. This assembly is then incorporated into an outer housing which is sealed to form the article for removing contaminants from a fluid. An example of such a final, nanomesh-containing, filter assembly prior inside an outer plastic housing is shown in FIG. 19.

Methods for Determining Effectiveness

Using established microbiological techniques, described herein, it has been demonstrated the carbon nanomesh filters are capable of removing more than 7 logs of a bacterial contaminant (*E. coli*) and more than 4 logs of a surrogate for viral agents (the MS 2 bacteriophage). These removal capacities exceed the requirements for bacterial removal and the recommended levels of viral removal specified by the US-EPA (*Guidance Manual for Compliance with the Filtration and Disinfection Requirements for Public Water Systems Using Surface Water*, U.S. Environmental Protection Agency, March 1991). Independent testing of the inventive article, it has confirmed that the article satisfies the basic standards for water purification in the United States.

Multiple tests were performed on samples made using the methods generally described above using bacteria, such as *E.coli*, and viruses, such as MS 2 bacteriophage. The MS 2 bacteriophage, which is commonly used as a surrogate in assessing a devices virus removal capabilities for drinking water, is a male specific, single stranded RNA virus, with a diameter of 0.025 µm and an icosahedral shape. Its size and shape are similar to other waterborne viruses such as the polio and hepatitis viruses, although the MS 2 bacteriophage is not a human pathogen.

The protocol used for testing the removal of the *E. coli* bacteria and the MS 2 bacteriophage from water in the all of the following examples were consistent with and generally adhered to: (i) Standard Operating Procedure for MS 2 bacteriophage Propagation/Enumeration. Margolin, Aaron, 2001, University of New Hampshire, Durham, N.H. and (ii) Standard Methods for the Examination of Water and Wastewater, 20$^{th}$ Edition, Standard Methods, 1998, APHA, AWWA, WEF, Washington, D.C., which are herein incorporated by reference.

Using these methods described above, and as exemplified in the following examples, strong adherence forces between bacteria and carbon nanotubes was observed. For example, the bacteria adhered to the carbon nanotubes surface, especially when dispersed during sonication. It is believed that the same adherence of *E. coli* suspension occurs when it is passed through the disclosed nanomesh of carbon nanotubes.

In addition, evidence that the integrity of the bacterial cell, may be partially compromised upon interaction with the carbon nanomesh was observed. For example, electron microscopy of the bacteria in the presence of carbon nanotubes described herein revealed images showing some apparent penetration of the bacterial shell/cell wall. After a prolonged period (24 hours) some disruption apparently resulted from a breech in the integrity of the cell wall, which, due to the difference in the osmotic pressure between the interior and exterior of the cell, led to a catastrophic failure of the cell wall and the disintegration of the bacteria. However, this disruption of cell integrity was apparent immediately upon contact with the carbon nanotubes, as observed by light microscopy in a phase microscope.

Further, tests confirmed the destruction of some bacteria, as evidenced by the presence of at least a small amount of free bacterial DNA and protein in the filtrate. However, most of the bacterial cells remain intact immediately after contact with the nanotubes. Although the inventive nanomesh article has been demonstrated to effectively remove bacteria from the effluent stream, the ability of the nanotubes to kill bacterial cells has not yet been established, although it is a likely possibility.

Further, through other testing of the inventive article other contaminants, such as those previously described (including metals, salts, organic contaminants, endotoxins) can be removed from water and air.

The invention will be further clarified by the following non-limiting examples, which are intended to be purely exemplary of the invention.

EXAMPLE 1

E. coli Interaction with Carbon Nanotubes

The interaction of an *E. coli* bacterial culture with a suspension of carbon nanotubes was investigated to determine the effectiveness of carbon nanotubes to attach to and subsequently disable or destroy bacterial cells. Further, this study will provide insight into the mechanisms active in the inventive nano-purification article. The procedure compared an untreated sample containing bacterial cultures to a sample mixed with carbon nanotubes. The comparisons will be done under high magnification using both light and atomic force microscopy techniques.

Preparation of *E. Coli* Suspension

An *E. coli* suspension was made by using a sterile, biological loop (commercially available) to remove a loop full of the reconstituted stock [obtained from American Type Culture Collection (ATCC), stock culture ATCC #25922] which was streaked on a commercially available blood agar plate. This plate was then incubated for 12-18 hours at 36° C., removed from the incubator and examined for purity.

Using a sterile biological loop (commercially available) one loop full of the incubated culture was removed and placed in 10 ml of sterile commercially available Tryptic soy broth (Remel cat. No. 07228). The *E. coli* was then grown in the resulting trypticase-soy broth for 18 hours at 37° C., followed by centrifugation and suspension, to form a concentrated bacterial culture of approximately $5 \times 10^9$ colony forming units(cfu)/ml in pure water.

Functionalization of Carbon Nanotubes with Nitric Acid

The carbon nanotubes were treated with nitric acid solution to remove contaminants (such as amorphous carbon, or catalyst particles and their supports which may interfere with the surface chemistry of the nanotube), increase the number of crystalline defect sites in the nanotubes and to attach carboxyl chemical group to these defect sites. This functionalization also provided a hydrophilic behavior to the carbon nanotubes.

The treatment was performed by mixing 250 mg of purified nanotubes in a total volume of 35 ml of concentrated nitric acid in a centrifuge tube, shaking well and sonicating in a Cole Parmer 8851 Sonicator at full power for 10 minutes in 50° C. water bath. The nitric acid/carbon nanotube mixture was then centrifuged at 2,500 rpm until the supernatant was clear (6-10 minutes) and then the supernatant was decanted. The nitric acid treatment was repeated, but with 20 minutes of sonication. The nitric acid treated carbon nanotubes were then water washed by suspending them in 35 ml total volume distilled water, sonicating (as above) for 10 min, centrifuging (as above), then decanting the supernatant. This water wash was repeated until the pH was at least 5.5 (~3-4 times), sonicating for 5 min each time.

Preparation of Test Solutions

The *E. coli* suspension, prepared as outlined above, was then divided into two equal parts. The untreated solution (Test Solution #1) was prepared by diluting one of the divided *E. coli* suspensions with distilled water to attain an *E. coli* concentration of $\sim 2 \times 10^9$ cfu/ml (2:5 dilution). The other solution (Test Solution #2) was prepared by adding 25 mg of functionalized nanotubes to the other divided *E. coli* suspension. This solution was then diluted with distilled water to achieve the same concentration of *E. coli* as in Test Solution #1. This dilution resulted in a concentration of carbon nanotubes in Test Solution #2 of 625 ppm.

Both Test Solutions #1 and #2 were simultaneously sonicated with a Branson-2510 Sonicator for 3 min. These Test Solutions were then centrifuged in a commercially available centrifuge at 2500 rpm for 2 minutes to form pellets, and the supernatant decanted leaving 1 ml of supernatant behind. The pellets of Test Solutions #1 and #2 were then used to make two samples (#1 and #2) described below.

Preparation of Sample #1: Carbon Nanotube Free

Sample #1 was prepared by placing a drop of the test solution free of carbon nanotubes (Test Solution #1) on a commercially available glass microscope slide (American Scientific Products, Micro Slides, plain, Cat. M6145, size 75×25 mm that was cleaned with sulfuric acid and rinsed with distilled water) and refrigerated at 4° C. for 19 hours. After refrigeration, atomic force microscopy (AFM) analysis was performed (without fixation) using a Veeco Dimension 3100 Scanning Probe System in tapping mode to investigate the sample.

Sample #1 was also thermally fixed (by brief exposure to an open flame) and then stained (with Gram Crystal Violet dye) followed by a water wash. Light microscopy was performed using an Olympus light microscope at 1000× magnification and under immersion oil. Digital images were made with an Olympus DP10 CCD.

Preparation of Sample #2: Carbon Nanotube Treated

Sample #2 was prepared by placing (and smearing) a drop of the carbon nanotube/*E. coli* test solution (Test Solution #2) on a glass microscope slide as described above. The sample was thermally fixed, stained, and light microscopy was conducted as for Sample #1 above. Sample #2 was then placed in a refrigerator at 4° C. for 19 hours, after which time it was removed and AFM analysis (as described above) was conducted as for Sample #1. Sample #2 was returned to the refrigerator for an additional 24 hours, after which time light microscopy was again conducted.

Results of Microscopic Analyses

Sample #1 (suspension of bacteria without carbon nanotubes) showed *E. coli* bacterial cells uniformly distributed over the entire surface of the slide (FIG. 14). The image further shows that the bacteria had well-defined edges, suggesting that the bacteria cells were intact. No changes in their shape were found after 2 days stored in a dry state in the refrigerator.

The results for samples from the carbon nanotube treated test solution (Sample #2) demonstrated bacteria clumped on the carbon nanotubes. (FIG. 15). The majority of the nanotubes were removed when the excess stain was washed from the slide. Bacteria concentration was observed at boundaries of the carbon nanotubes.

There were numerous individual bacterial cells present over the entire slide for the sample without carbon nanotubes (Sample #1) bacterial cells were absent from most of the slide for the sample with carbon nanotubes (Sample #2). As shown in FIG. 15, any bacteria that were present in the latter case were tightly packed around the carbon nanotubes, indicating that the carbon nanotubes were capturing and holding the bacteria.

Sample #1 demonstrated *E. coli* closely packed together. As shown in FIG. 16, the bacterial cells of normal cells have sharp boundaries. The decrease in size and packing density of bacteria was seen in the AFM image of sample #1 before heat treatment and optical image of this sample after heat treatment.

Sample #2 showed some cells in the vicinity of the nanotubes, with the boundary of the *E. coli* cell walls being diffused and/or damaged. In fact, after mixing with the nanotubes, some of the *E. coli* cells disintegrated beyond the point of recognition. The presence of some diffused *E. coli* fragments was also seen in the vicinity of the nanotubes.

On sonication of *E. coli* and functionalized carbon nanotubes in distilled water, the two components agglomerated. This is thought to be due to electrostatic and Van Der Waals forces which act at the nanoscale. To the limit of detection, it was observed that all bacteria in suspension were in contact with the nanotubes, and adhered. There were no longer free *E.coli* cells in Solution #2. This illustrated the ability of the dispersed carbon nanotubes to strongly attach to and immobilize bacteria.

The disintegration of the *E. coli* cells, when it was noted, appeared after the cells came into intimate contact with the nanotubes. As a result, these bacteria cells appeared to lose their sharp cell boundaries and their internal contents appeared to spill out from the cell. For example, FIG. 17 shows a scanning electron micrograph (SEM) image of a bacterial cell that burst upon interaction with a carbon nanotube.

In the cells affected, the beginning of this process was noted after 3 hours, and after 22 hours the internal contents spread so far that it was difficult to distinguish the shape of the cell.

A highly motile bacterium, *Pseudomonas flourescens*, grown for 12 hours in nutrient broth (from Difco Laboratory) at room temperature, was mixed with a solution of carbon nanotubes. Viewed under a dark field microscope, we observed the motile bacteria swim near and get pulled into the aggregated carbon nanotubes and become firmly attached to the exposed carbon nanotube fibers. Within 5 minutes of contact, the entire surface of the carbon nanotube aggregate was covered with hundreds of intact bacteria, which were obviously firmly attached since they appeared to struggle, but were unable, to leave. These bacteria lost all motility and became completely rigid within 30 seconds of initial contact with carbon nanotube fibers. This indicated the capacity of the finely dispersed carbon nanotubes fibers to rapidly attach to and immobilize large numbers of bacteria. This confirms the basis for the effectiveness of carbon nanotube filters in removing microorganisms.

EXAMPLE 2

Cylindrical Purification Article

Construction of Cylindrical Purification Article:

Iron Hydroxide Treated Glass Fiber Preparation

A solution of 23.5 liters of distilled water and 9.62 ml of 10N sodium hydroxide (NaOH) was made and stirred for 1 hour. A quantity of 16.66 grams of Ferric Chloride ($FeCl_3 \cdot 6H_2O$) was added and stirred until a final pH of ~2.2 was reached (~24 hours). To this solution, 200 grams of glass fibers of size 100-500 nm in diameter and 300-500 μm in length (Johns-Mansville) were added and stirring was continued until solution was clear of iron (~3 hours). The solution was diluted with distilled water to obtain a glass fiber concentration of 10 grams/liter.

Preparation of Depositional Suspension

A suspension was prepared using a solution of functionalized carbon nanotubes and iron hydroxide treated glass fibers previously prepared as described above. To prepare the component parts of the suspension, 5 g of the functionalized carbon nanotubes (carboxylated through the nitric acid wash procedure described in Example #1) were suspended in 1 liter of water and placed in a room temperature water bath in a Cole Parmer 8851 Sonicator and sonicated at full power for 20 minutes. Four liters of distilled water were added to the sonicated, functionalized carbon nanotubes/water mixture to yield a concentration of 1 mg functionalized carbon nanotubes per 1 ml water. Approximately 100 ml of Fe decorated glass fiber solution was placed in a separate container and diluted to 1 liter with distilled water. This mixture was blended in a commercial blender for 5 minutes.

To mix the first depositional suspension, 600 ml of the suspended functionalized carbon nanotubes (described above) were added to 960 ml of the glass fiber solution (5:8 CNT/glass ratio by weight). This mixture was diluted to 4 liters by adding a quantity sufficient amount of distilled water, and sonicated with a Branson model 900B probe Sonicator for 10 minutes on full power.

Deposition of Carbon Nanomesh

The structure of the final nanomesh was achieved by depositing a layer of the functionalized carbon nanotubes/iron hydroxide coated glass fiber mixture onto a carbon block substrate.

The procedure for depositing the functionalized carbon nanotube/iron hydroxide coated or decorated glass mixture is schematically represented in FIG. 18. A filter assembly was made by loading a cylindrical carbon block onto a perforated mandrel. The deposition chamber was filled with the carbon nanotube/glass fiber suspension (5:8 ratio). The filter assembly was connected to vacuum tubing leading to a Franklin Electronics Varian TriScroll vacuum pump and then was submerged in the filled deposition chamber. The vacuum pump attached to the filter assembly was turned on and the entire suspension was drawn through the carbon filter substrate under vacuum, depositing a nanomesh on its outer surface. After deposition, the deposited filter assembly was removed from the deposition chamber, remained connected to the vacuum pump and the deposited nanomesh filter assembly was dried under vacuum for 1-2 hours in a drying oven set at 50° C. within a nitrogen atmosphere.

The fully assembled filter article was comprised of a central carbon filter core coated with the functionalized carbon nanotube nanomesh and covered by a porous protective paper held in place with cylindrical plastic netting. This cartridge was capped and the edges of the nanomesh sealed to prevent fluid circumventing the nanomesh and placed into an outer housing to create the final product (FIG. 19).

Effectiveness of Cylindrical Purification Article:

As a fluid purification test of the cylindrical form of the inventive article on water contaminated was conducted with an *E. coli* bacterial culture [obtained from American Type Culture Collection (ATCC)].

A bacterial assay was conducted by challenging the nanomesh, made in accordance with the present example (Example 2), with a challenge fluid of reconstituted *E. coli* stock culture ATCC #25922. This challenge fluid was made by using a sterile biological loop (commercially available) to remove a loop full of the reconstituted stock and streaking it on a commercially available blood agar plate. This plate was then incubated for 12-18 hours at 36° C. The culture was then removed from the incubator and examined for purity.

Using a sterile biological loop (commercially available) one loop full of the incubated culture was removed and placed in 10 ml of sterile commercially available Tryptic soy broth (Remel cat. No. 07228). *E. coli* was then grown in the resulting trypticase-soy broth 18 hours at 37° C. to form a culture of approximately $1 \times 10^9$ colony forming units (cfu)/ml. A 1 ml sample of this stock culture was added to 100 ml of water to be used for the challenge test, thereby diluting the concentration to approximately $1 \times 10^7$ cfu/ml. The resulting challenge water was then passed through the Cylindrical Purification Article.

The test was performed in accordance with the "*Standard Methods for the Examination of Water and Waste Water*" cited above. Results of tests following the protocols described above established consistent removal of *E. coli* bacteria greater than 6 logs (>99.99995%) to greater than 7 logs (>99.999995%) when the challenge fluid was passed through the inventive nanomesh. These test results established removal rates which exceeded EPA potable water standards (referenced above) for removal of bacteria from water. The EPA standards dictate 6 logs removal (>99.99995%) of *E. coli* bacteria to achieve potable water. Improved purification by greater log removals of *E. coli* bacteria have been achieved in such tests, by passing a solution of known bacterial concentration (i.e. challenging) the nanomesh with higher concentrations of *E. coli* bacteria challenge suspension, made as described above. Such tests with higher concentrations confirm removal rates of greater than 7 log (>99.999995%). Independent tests of the nanomesh, using the test procedures described in this example, establish this material as a barrier to *E. coli* bacteria. Further, independent laboratory tests results showed more than 6 logs of removal of different test bacteria (*Klebsiella terrigena* and *Brevindomonas*), confirming that the material is a general barrier to bacteria.

EXAMPLE 3

Fabrication of a Flat Purification Article

Analogously to Example 2, a flat nanomesh was made from commercially available purified carbon nanotubes and a non-woven, fused, polypropylene fabric substrate. To begin, 100 mg of functionalized carbon nanotubes (carboxylated through a nitric acid wash as described in Example #1) were then added to 400 ml of commercially available neat isopropanol and sonicated in a "Branson 900B Ultrasonicator" at 80% power until the carbon nanotubes were well dispersed (about 10 minutes). The mixture was further diluted by adding 2 liters isopropanol such that the total volume of the resulting mixture was 2.4 liters. This diluted mixture was sonicated for an additional 10 minutes.

Next, 800 mg of a commercially available 200 nm diameter glass nano-fiber was homogenized in a commercially available blender at full power for 10 minutes in 500 ml of the commercially available neat isopropanol. The homogenized mixture was then diluted by adding an additional 1 liter of commercially available neat isopropanol.

The mixtures of carbon nanotubes and glass nano-fibers were combined and then quantity sufficient (Q.S.) amounts of isopropanol was added to obtain 4 liters. This 4 liter solution was then sonicated with a "Branson 900B Ultrasonicator" at 80% power for 15 minutes, which caused the carbon nanotube nanomaterial to uniformly disperse.

The entire 4 liter solution was then drawn through a commercially available 5 micron, non-woven, fused activated carbon fabric under a differential pressure of 1 atmosphere to deposit the carbon nanotube/treated glass fiber nanomesh. The resulting nanomesh was removed from the fabricator and allowed to dry in an oven at 50° C. for 2 hrs.

The resulting flat, square nanomesh/substrate membrane is glued, using an NSF compliant hot-melt adhesive, into one side of a flat housing. This half of the housing is then mated and glued to its companion to seal. The structure of the resulting device is represented schematically in FIG. 13.

Test of Effectiveness of Flat Purification Article:

a) Water Contaminated with *E. coli*—Chemical Analysis

The following describes the results of a chemical analysis of filtrate from an *E. coli* challenge test, performed as described in Example 2, on the Flat Nanomesh Purification Article made in accordance with present example. This example provided some evidence for some amount of destruction of *E. coli* bacteria passing through the inventive nanomesh. This evidence of partial destruction of the contaminant (*E. coli* bacteria) was established by the presence of bacterial DNA and proteins in the challenge filtrate.

A challenge test was run following the same procedures as in Example 2, except that the composition of the challenge solution was ~$1 \times 10^8$ cfu/ml of *E. coli*. A total of 100 ml (total ~$1 \times 10^{10}$ cfu) of this challenge solution was drawn through the carbon nanomesh/substrate material using a differential pressure of ~0.25 psi. A control filtrate was obtained by passing the *E. coli* challenge filtrate through a commercially available 0.45 micron Millipore filter. The test challenge filtrate was not concentrated. The resulting filtrates, of the control and the challenge, were then analyzed with a commercially available spectra-photometer to determine the presence of protein and DNA. However, the analysis of the filtrate with a commercially available spectra-photometer revealed 40 µg/ml of DNA and 0.5 mg/ml of protein. Concentrations of protein and DNA at these levels in non-concentrated challenge filtrate were 6 times higher than the control test material obtained by filtration through a Millipore filter. These concentrations confirmed the destruction of at least some portion of the added *E. coli* by the nanomesh.

b) Water Contaminated with MS-2 Bacteriophage Virus

The Flat Purification Article, made in accordance with the present example (Example 3) was tested with water contaminated by MS-2 bacteriophage virus using the procedure described above and in the "*Standard Operating Procedure for MS-2 Bacteriophage Propagation/Enumeration*, Margolin, Aaron, 2001, An EPA Reference Protocol." MS-2 bacteriophage virus is commonly used in assessing treatment capabilities of membranes designed for treating drinking water (NSF 1998). The pressurized challenges for this example were performed with 100 ml challenge solutions using the protocols described above. The MS-2 challenge materials were prepared in accordance with those steps enumerated above.

In this test, eighty (80) membranes comprised of the carbon nanotube nanostructured material made in accordance with the present example (Example 3), were challenged. The challenge material used was water contaminated with MS-2 bacteriophage virus to the concentration of approximately $5 \times 10^6$ plaque forming unit (pfu)/ml.

Of the 80 units tested, 50 units achieved MS-2 removal of 5 logs (99.999%) or greater than 5 logs (>99.9995%). The remaining 30 units demonstrated 4 logs (99.99%) or greater than 4 logs (>99.995%) removal of MS-2. While EPA standards recommend 4 logs removal of MS-2 Bacteriophage to achieve potable water, it is believed that better sensitivity (higher log removal) can be achieved by challenging with higher log challenges of MS-2. Improved purification by greater log removals of MS-2 Bacteriophage have been achieved in such tests, by challenging the carbon nanotube nanomesh, made in accordance with the present example (Example 3), with higher concentrations of MS-2 Bacteriophage challenge suspension, made as set forth above. Independent tests of the carbon nanomesh article, made in accordance with the present example (Example 3), establish this material as a barrier to MS-2 Bacteriophage.

c) Water Contaminated with Arsenic (As)

The Flat Purification Article, made in accordance with the present example (Example 3), with water contaminated with arsenic. In this test, a 100 ml water solution containing ~150 ppb (parts per billion) arsenic was passed through the carbon nanomesh made in accordance with the present example (Example 3). A sample of the arsenic treated water was analyzed according to the EPA Method #SM 183113B. The analysis of the challenge filtrate confirm a reduction of the arsenic level by 86%±5%; after passing the challenge arsenic treated water, once through the inventive carbon nanomesh material.

d) Aircraft Fuel Contaminated with Bacteria

The Flat Purification Article, made in accordance with the present example (Example 3), was tested for contaminated jet fuel. A sample of contaminated jet fuel (JP8) was obtained from a 33,000 gallon storage tank located at the United States Air Force Research facility at the Wright Patterson Air Force base. After collection, the sample was cultured on trypticase-soy agar and found to contain three types of bacteria: two *Bacillus* species and one *Micrococcus* species. The sample was separated in two containers of 2 liters each. Both containers presented two distinct layers, jet fuel on top and water on the bottom. Container A contained a heavy contaminated growth layer at the interface between the water and the fuel. Container B only showed slight contamination. The challenge test bacteria were obtained from the interface of the fuel and water from Container B.

After being homogenized, which was accomplished by shaking the challenge test fuel/water/bacteria vigorously for 1 minute, 200 ml of the fuel/water/bacteria challenge mixture was passed one time, using ~1.5 psi differential pressure, through the carbon nanotube, nanostructured material, made in accordance with the present example (Example 3).

The fuel/water/bacteria challenge filtrate sample was allowed to separate into its fuel—water components, and four test samples were obtained from each component. Each test sample was plated on agar. Samples were then incubated to analyze bacteria growth at 37° C. and samples were incubated at room temperature to analyze mold growth. No bacteria or mold culture growth was observed on the challenge filtrate test plates after incubating the samples for 24 and 48 hours. The control samples presented vigorous colonies of bacteria and mold growth after incubation at 24 and 48 hours. The results confirm that the carbon nanomesh, made in accordance with the present example (Example 3), was a barrier to bacteria in fuel for it accomplished removal of bacteria and mold from the fuel beyond the limits of detection with testing protocols.

EXAMPLE 4

Flat Purification Article using a Multistep Functionalization

A flat nanomesh device was made from commercially available, purified, carbon nanotubes and a non-woven, fused, 0.5 oz/yd² carbon tissue paper substrate. The construction of this device utilized a process of self assembly of the nanomesh, as defined above. Specific electropositive and electronegative functional components were used to enable this self assembly. The carbon nanotubes were functionalized with amine groups which caused them to be electropositive (i.e. positive zeta potential) when dispersed in water. The glass fibers were decorated with iron hydroxide clusters that caused them to be electronegative when dispersed in water. As shown in FIG. 22, when the two suspensions were combined, the nanotubes wrapped around the glass fibers due to electrical forces.

To begin, 20 g of carbon nanotubes were refluxed with 400 ml of 60% 36N sulfuric acid and 40% 15.8N nitric acid at 110° C. for 30 minutes. This is known to add carboxyl functional groups to the carbon nanotubes. These carboxyl functionalized nanotubes were filtered, washed in distilled water and then dried in an oven at 100° C. The dry nanotubes were then suspended in 500 ml thionyl chloride and sonicated 20 hours at 60° C. The thionyl chloride was distilled off and the carbon nanotube sample was dehydrated using a vacuum pump. The dehydrated nanotubes were suspended in 500 ml of ethylenediamine and sonicated for 20 hours at 60° C. in a nitrogen atmosphere. The ethylenediamine was distilled off and the sample washed with 0.1M hydrochloric acid, filtered and rinsed repeatedly with distilled water until a neutral pH is reached. The rinsed amine functionalized carbon nanotubes were then dried in an oven at 100° C. for 24 hours.

A mixture of 360 mg of amine functionalized carbon nanotubes and 960 mg of treated glass fibers were combined and then a quantity sufficient (Q.S.) amount of distilled water was added to obtain 4 liters. This 4 liter solution was then sonicated with a "Branson 900B Ultrasonicator" at 80% power for 15 minutes, which caused the carbon nanotube/glass fiber nanomaterial to uniformly disperse.

The entire 4 liter solution was then drawn through a commercially available, non-woven, fused, 0.5 oz/yd² carbon tissue under a differential pressure of ~1 atmosphere to deposit the self-assembled, carbon nanotube/treated glass fiber nanomesh. The resulting nanomesh was removed from the fabricator and allowed to dry in an oven at 50° C. for 2 hours.

The resulting flat, square nanomesh/substrate membrane is glued, using an NSF compliant hot-melt adhesive, into one side of a flat housing. This half of the housing is then mated and glued to its companion to seal. The structure of the resulting device is represented schematically in FIG. 13.

Test of Effectiveness of Flat Purification Article:

The flat purification device constructed in the present example (Example #4) using the amine functionalized carbon nanotubes and iron hydroxide decorated glass fibers was tested for biological removal as in described in the Tests of Effectiveness for Example #3 [test a) *E. coli* and b) MS-2 bacteriophage]. These tests demonstrated that the self-assembled nanomesh article achieved a removal capability for bacteria and virus of over 8 logs and 7 logs, respectively.

EXAMPLE 5

Fluid Desalination

A 64 layer, flat nanomesh device was made from: commercially available purified, functionalized carbon nanotubes; glass fibers measuring 100-500 nm in diameter and 300-500 µm in length; a solution of 0.0125% by weight of polyvinyl alcohol with a molecular weight of 20,000 g in distilled water; 1.5 oz/yard cellulose filter paper as an insulator; a non-woven, fused, 0.5 oz/yard$^2$ conductive carbon tissue paper substrate; silver-imbedded conductive and insulating epoxies; a plastic, non-conductive housing; and a power supply to supply 1.5V DC across each neighboring pair of conducting nanomesh layers.

To begin, 25 mg of functionalized nanotubes (carboxylated through a nitric acid wash procedure as described in Example #1) and 50 mg of glass fiber (described above) were suspended in 4 liters of distilled water containing a 0.0125% concentration of polyvinyl alcohol as listed above. The suspension was stirred for 3 minutes using an IKA UltraTurrax T18 immersion blender at speed 3.

This carbon nanotube/glass fiber suspension was deposited on a 5"×5" area of a 5.5"×5.5" sheet of 0.5 oz/yard$^2$ carbon tissue paper using differential pressure of ~1 psi. Four 2" diameter discs were cut from this 5"×5" nanomesh sheet, thereby completing 4 layers of the 64 layer, 2" diameter device (32 of the 64 layers are conductive, the others are insulating).

An electrical lead was attached to each conductive nanomesh layer using a silver-filled conductive epoxy. All conductive nanomesh layers were sandwiched between insulating layers and these "sandwiches" were then stacked with the electrical leads being equally spaced azimuthally (i.e. rotated ~11.25° from the leads on the layer above and below). The electrical leads were bundled and routed through the plastic housing wall to the power supply and the entire assembly was sealed (an example of a 16 conducting layer version of a prototype desalination device is shown in FIG. 20).

A static retention test was performed by flowing 1 liter of a 1‰ saline solution (1‰=1 g salt/1000 g water) through the device with no electrical charge or stimulation imposed. The filtrate was tested for salt content and it was found to have lost ~13 mg of salt. Therefore the inventive device in static mode (i.e. no electronic stimulation) reduced the salinity by ~1.3%. This reduction amounted to 0.42 grams of salt removed per gram of carbon nanotubes in the inventive device.

A dynamic retention test was performed, wherein a differential DC voltage of 4.0 mV was applied to each of 16 neighboring pairs of conductive nanomesh layers (i.e. even numbered nanomesh layers were positively charged and odd numbered layers were negatively charged). A saline challenge solution of 1 g of sodium chloride dissolved in 1000 ml of distilled water (1‰ salinity) was used to test the efficacy of the device. In one pass through the device, 1.6% of the salt was removed. This removal rate was equivalent to 0.52 g of salt per g of carbon nanotubes. This represented a 23% increase in salt removal over the static device, showing that even a very weak voltage enhanced the removal of salt ions from a water solution, thereby demonstrating the nano-electric removal effect. Further enhancement of the salt removal will certainly be achieved as the DC voltages are increased and AC signals, which disrupt the DeBye atmosphere, are imposed.

EXAMPLE 6

Air Membrane

A flat air membrane filter was constructed using functionalized carbon nanotubes (carboxylated through the nitric acid wash as described in Example #1). The procedure suspended 25 mg of these functionalized nanotubes in 25 ml of distilled water and sonicated for 10 minutes in a Branson Model 900B Sonicator in a water bath at room temperature. This solution was then diluted to 4 liters with distilled water and polyvinyl alcohol was added so that a concentration of 0.125% polyvinyl alcohol by weight was achieved. The suspension was then mixed for 3 minutes at speed setting 3 with an UltraTurrax T18 Basic immersion blender. The nanomesh was created by deposition on a 5"×5" area of a 5.25"×5.25" square piece of porous, polymeric substrate using a differential pressure filtration process with a differential pressure of ~1 psi.

Test of Effectiveness of Air Membrane Article:

Biological removal testing was performed on the membrane to determine its effectiveness. Two 2.5" discs were cut from the square membrane and were mounted between two flat metal rings of 2" ID, 2.5" OD. One disc was used to measure the pressure drop versus flow speed curves for the membrane article device, while the other was used for biological removal testing. The bio-removal testing was done by mounting the filter disc in a 2" ID cylindrical wind tunnel (schematically shown in FIG. 21) which was capable of testing the capture efficiency of bacterial spores of *Bacillus subtilis*, a widely accepted surrogate for biological agents but not a human pathogen, making it safe for laboratory testing.

The testing entailed releasing the bacterial spores upstream of the filter disc through an aerosolizer and capturing the fraction that passed through the filter in a fluid-filled, all-glass impinger at the downstream end of the testing apparatus. A controlled set of experiments were performed to estimate the spore retention of the testing apparatus. In this biological testing, we achieved over 6 logs of removal of *Bacillus subtilis* spores. Further, we were able to determine that removal of biological agents is independent of the removal of non-biological particles and of the filter's resistance to air flow.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An article for removing contaminants from a fluid, said article comprising carbon nanotubes, at least one of which comprises at least one molecule or cluster attached thereto or located therein, wherein the carbon nanotubes are present in the article in an amount sufficient to reduce the concentration of contaminants in fluid that comes into contact with the article and are in the form of an assembled nanomesh in which the carbon nanotubes are connected or attached to other carbon nanotubes, to fibers, to particles, or any combination thereof.

2. The article of claim 1, further comprising a ridged or flexible, porous support substrate.

3. The article of claim 2, wherein the porous support substrate comprises a material chosen from ceramics, carbon or carbon based materials, metals or alloys, nonmetals, and plastics, and fibrous materials, said fibrous materials being woven or non-woven or any combination thereof.

4. The article of claim 1, wherein at least one molecule or cluster comprises an inorganic compound containing at least one metal atom chosen from: lithium, sodium, magnesium, aluminum, potassium, calcium, scandium, titanium, vanadium, chromium, manganese, iron, cobalt, nickel, copper, zinc, gallium, rubidium, strontium, yttrium, zirconium, niobium, molybdenum, rhodium, palladium, silver, indium, tin, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, bismuth and at least one nonmetal atom chosen from: hydrogen, boron, carbon, nitrogen, oxygen, fluorine, silicon, phosphorus, sulfur, chlorine, bromine, antimony, iodine and combinations thereof.

5. The article of claim 1, wherein the cluster comprises quantum dots.

6. The article of claim 1, wherein at least one molecule or cluster comprises an organic compound comprising one or more proteins, carbohydrates, polymers, aromatic or aliphatic alcohols, and nucleic acid.

7. The article of claim 1, wherein at least one cluster comprises at least one microorganism, tissue cell, bacteria, or nanobacteria.

8. The article of claim 1, wherein at least one molecule or cluster comprises an organic compound comprising one or more chemical group chosen from carboxyls, amines, arenes, nitriles, amides, alkanes, alkenes, alkynes, alcohols, ethers, esters, aldehydes, ketones, polyamides, polyamphiphiles, diazonium salts, metal salts, pyrenyls, thiols, thioethers, sulfhydryls, silanes, and combinations thereof.

9. The article of claim 1, wherein the assembled nanomesh comprises carbon nanotubes and glass fibers.

10. The article of claim 1, wherein the fiber is chosen from:
(a) polymeric material chosen from single or multi-component polymers chosen from nylon, acrylic, methacrylic, epoxy, silicone rubbers, polypropylene, polyethylene, polyurethane, polystyrene, polycarbonates, aramids, polychloroprene, polybutylene terephthalate, poly-paraphylene terephtalamide, poly (p-phenylene terephtalamide), and polyester ester ketone, polyesters, polytetrafluoroethylene, polyvinylchloride, polyvinyl acetate, viton fluoroelastomer, polymethyl methacrylate, polyacrylonitrile, and combinations thereof;
(b) ceramic material chosen from boron carbide, boron nitride, boron oxide, spinel, garnet, lanthanum fluoride, calcium fluoride, silicon carbide, carbon and its allotropes, glass, quartz, alumina, aluminum nitride, aluminum hydroxide, zirconium oxide, zirconium carbide, zirconium boride, zirconium nitride, hafnium boride, thorium oxide, yttrium oxide, magnesium oxide, cordierite, mullite, silicon nitride, ferrite, sapphire, steatite, titanium carbide, titanium nitride, titanium oxide, titanium boride, and combinations thereof;
(c) at least one metallic material chosen from aluminum, boron, copper, cobalt, gold, platinum, palladium, silicon, steel, iridium, indium, iron, rhodium, palladium, gallium, germanium, tin, titanium, tungsten, nickel, niobium, magnesium, manganese, molybdenum, silver, zirconium, yttrium, their oxides, hydrides, hydroxides and alloys thereof;
(d) at least one biological material or derivative thereof chosen from silk fiber, cotton fiber, wool fiber, flax fiber, feather fibers, cellulose fiber extracted from wood, legumes or algae;
(e) at least one carbon nanotube chosen from single walled, double walled or multi-walled carbon nanotubes that have either a nested or non-nested morphology of nano-horns, nano-spirals, nano-springs, dendrites, trees, spider nanotube structures, nanotube Y-junctions, and bamboo morphology or multi-stranded helices; and
(f) at least one metallic oxide or metallic hydroxide nanowire.

11. The article of claim 1, wherein the fibers have a diameter ranging from 1 nm to 1 cm, and possess aspect ratios (length/diameter) from 2 to $10^9$.

12. The article of claim 1, wherein at least one carbon nanotube is chosen from single walled, double walled or multi-walled carbon nanotubes that have either a nested or non-nested morphology of nano-horns, nano-spirals, nano-springs, dendrites, trees, spider nanotube structures, nanotube Y-junctions, bamboo morphology, multi-stranded helices, multi-stranded nested helicies, or nested helicies.

13. The article of claim 1, wherein said contaminants comprise one or more bacteria, viruses, oocysts, spores, molds, coliforms, parasites, pollens and fungi.

14. The article of claim 13, wherein the bacteria comprise anthrax, typhus, or cholera, the viruses comprises smallpox and hepatitis.

15. The article of claim 1, wherein said contaminants comprise one or more biological molecules chosen from DNA, RNA, and natural organic molecules.

16. The article of claim 1, wherein said contaminants comprise one or more chemical compound chosen from natural and synthetic organic molecules, inorganic contaminants, pharmaceuticals and ions.

17. The article of claim 16, wherein said natural and synthetic organic molecules are chosen from toxins, endotoxins, proteins, enzymes, pesticides, and herbicides, said inorganic contaminants are chosen from heavy metals, cleaning agents, fertilizers, inorganic poisons, said pharmaceuticals are chosen from medicines, solvents, reagents, and said ions are chosen from salt in seawater and airborne particles.

18. The article of claim 1, wherein at least one contaminant comprises at least one atom or ion chosen from the elements: antimony, arsenic, aluminum, selenium, hydrogen, lithium, boron, carbon, oxygen, calcium, magnesium, sulfur, chlorine, niobium, scandium, titanium, vanadium, chromium, manganese, iron, cobalt, nickel, copper, zinc, gallium, germanium, bromine, strontium, yttrium, zirconium, molybdenum, rhodium, palladium, iodine, silver, cadmium, indium, tin, cesium, barium, lanthanum, tantalum, beryllium, copper, fluoride, mercury, tungsten, iridium, hafnium, rhenium, osmium, platinum, gold, mercury, thallium, lead, bismuth, polonium, radon, radium, thorium, uranium, plutonium, and radon.

19. The article of claim 1, wherein the fluid comprises:
(a) a liquid chosen from water, petroleum and its byproducts, biological fluids, foodstuffs, alcoholic beverages, and pharmaceuticals, or
(b) a gas chosen from air, industrial gases, and smoke from a vehicle, smoke stack, chimney, or cigarette, wherein said industrial gases comprise argon, nitrogen, helium, ammonia, and carbon dioxide.

20. The article of claim 1, further comprising multiple distinct layers of carbon nanotubes, wherein each layer reduces the amount of a different contaminant.

21. The article of claim 1, further comprising multiple distinct layers of carbon nanotubes, wherein there is a voltage differential between at least two of the layers.

22. The article of claim 21, wherein either AC voltages, DC voltages or combinations thereof, are applied, to at least one of said layers of carbon nanotubes to aid in the removal, separation, immobilization and/or destruction of contaminants.

23. The article of claim 22, wherein the voltage comprises AC voltage having a frequency and amplitude signal that is sufficient to disrupt the DeBye atmosphere surrounding at least one charged contaminant in said fluid.

24. The article of claim 23, wherein said charged contaminants are ions comprising the salt in sea and brackish waters.

25. The article of claim 23, wherein said ions comprise sodium, chloride, potassium, calcium, magnesium, sulfate, bicarbonate, manganese, iron, copper, mercury, gold, silver, platinum, lead, arsenic, uranium, and palladium.

26. The article of claim 23, wherein the charged contaminants are ions found in fresh water, wastewater and effluent streams.

27. The article of claim 24, wherein at least one of said multiple layers is sufficient to desalinate water and at least one other layer is sufficient to remove, separate, immobilize and/or destroy other contaminants.

28. The article of claim 27, wherein said other contaminants comprise one or more pathogens, viruses, microbiological organisms, DNA, RNA, natural organic molecules, molds, fungi, natural and synthetic toxins, heavy metals, endotoxins, proteins, prions, and enzymes.

29. The article of claim 27, wherein said other contaminants comprise at least one atom or ion chosen from antimony, arsenic, aluminum, selenium, hydrogen, lithium, boron, carbon, oxygen, sodium, calcium, magnesium, sulfur, chlorine, niobium, scandium, titanium, vanadium, chromium, manganese, iron, cobalt, nickel, copper, zinc, gallium, germanium, bromine, strontium, yttrium, zirconium, molybdenum, rhodium, palladium, iodine, silver, cadmium, indium, tin, cesium, tungsten, iridium, hafnium, rhenium, osmium, platinum, gold, mercury, thallium, lead, polonium, radon, radium, thorium, uranium, and plutonium.

30. The article of claim 1, wherein said fluid is water.

31. The article of claim 1, wherein said fluid comprises air.

32. The article of claim 1, further comprising at least one fiber chosen from glass, quartz, alumina, and aluminum hydroxide.

33. A method of reducing the amount of contaminants in a fluid, said method comprising:
(a) contacting a fluid with an article comprising carbon nanotubes, a majority of which comprise at least one molecule or cluster attached thereto or located therein, wherein the carbon nanotubes are present in the article in an amount sufficient to reduce the concentration of at least one contaminant in fluid that comes into contact with the article and are in the form of an assembled nanomesh in which the carbon nanotubes are connected or attached to other carbon nanotubes, to fibers, to particles, or any combination thereof, and
(b) removing at least one contaminant from the fluid.

34. The method of claim 33, wherein the article comprises multiple distinct layers of said carbon nanotubes.

35. The method of claim 33, wherein each of said multiple distinct layers reduces the amount of a different contaminant.

36. The method of claim 33, further comprising multiple distinct layers of carbon nanotubes, wherein there is a voltage differential between at least two of the layers.

37. The method of claim 36, wherein either AC voltages, DC voltages or combinations thereof, are applied, to at least one of said layers of carbon nanotubes to aid in the removal, separation, immobilization and/or destruction of contaminants.

38. The method of claim 37, wherein the voltage comprises AC voltage having a frequency and amplitude signal that is sufficient to disrupt the DeBye atmosphere surrounding at least one charged contaminant in said fluid.

39. The method of claim 37, wherein the DC voltage differential is in the range from greater than 0.0 to 200 kV.

40. The method of claim 37, wherein the AC voltage peak-to-peak amplitude is in the range from greater than 0.0 to 200 kV.

41. The method of claim 37, wherein the AC frequency is in the range of 1.0 millihertz to 1.0 terahertz.

42. The method of claim 38, wherein said charged contaminants are ions comprising the salt in sea and brackish waters.

43. The method of claim 33, wherein said ions comprise sodium, chloride, potassium, calcium, magnesium, sulfate, bicarbonate, manganese, iron, copper, mercury, gold, silver, platinum, lead, arsenic, uranium, and palladium.

44. The method of claim 43, wherein the charged contaminants are ions found in fresh water, wastewater and effluent streams.

45. The method of claim 33, wherein the fluid comprises salt water, and at least one of said multiple layers is sufficient to desalinate water and at least one other layer is sufficient to remove, separate, immobilize and/or destroy other contaminants in said salt water.

46. The method of claim 45, wherein said other contaminants comprise one or more pathogens, viruses, microbiological organisms, DNA, RNA, natural organic molecules, molds, fungi, natural and synthetic toxins, heavy metals, endotoxins, proteins, prions, and enzymes.

47. The method of claim 45, wherein said other contaminants comprise at least one atom or ion chosen from antimony, arsenic, aluminum, selenium hydrogen, lithium, boron, carbon, oxygen, sodium, calcium, magnesium, sulfur, chlorine, niobium, scandium, titanium, vanadium, chromium, manganese, iron, cobalt, nickel, copper, zinc, gallium, germanium, bromine, strontium, yttrium, zirconium, molybdenum, rhodium, palladium, iodine, silver, cadmium, indium, tin, cesium, tungsten, iridium, hafnium, rhenium, osmium, platinum, gold, mercury, thallium, lead, polonium, radon, radium, thorium, uranium, and plutonium.

48. The method of claim 33, wherein said fluid is water.

49. The method of claim 33, wherein said fluid comprises air.

50. The method of claim 33, further comprising at least one fiber chosen from glass or alumina.

51. A method of preparing a nanomesh material comprising carbon nanotubes, said method comprising:
(a) treating the carbon nanotubes by exposing the carbon nanotubes to at least one chemical, radiative or mechanical treatment;
(b) rinsing the carbon nanotubes in at least one solvent chosen from aqueous, inorganic, and organic solvents;
(c) forming a suspension of carbon nanotubes by mixing said carbon nanotubes with at least one solvent chosen from aqueous, inorganic, and organic solvents, said suspension optionally containing fibers, particles or combinations thereof, wherein one or more carbon nanotubes comprise at least one molecule or cluster attached thereto or located therein; and (d) depositing the suspension onto a porous substrate to form a nanomesh layer of carbon nanotubes on the porous substrate, wherein the carbon nanotubes are connected or attached to other carbon nanotubes, to said fibers, to said particles, or any combination thereof.

52. The method of claim 51, wherein said chemical treatment comprises a treatment with an oxidizer, said radiative treatment comprises at least one of microwave, E-beam, and heat treatment, and said mechanical treatment comprises at least one of sonication and stirring.

53. The method of claim 51, wherein said treatment of (a) is in an amount sufficient to create defects, said carbon nanotubes comprising at least one functional group attached to at least one of said defects or to a non-defective surface of said carbon nanotubes.

54. The method of claim 51, wherein the attachment of functional chemical groups to the carbon nanotubes are in an amount sufficient to adjust the zeta potential of the resulting functionalized carbon nanotube.

55. The method of claim 51, wherein the carbon nanotubes are multi-walled and have a length ranging from 0.1 μm to 100 mm, and a diameter ranging from 1 to 300 nm.

56. The method of claim 52, wherein the oxidizer comprises one or more oxidizer chosen from nitric, sulfuric, hydrochloric or hydrofluoric acids, potassium permanganate, hydrogen peroxide or a mixture thereof, in an amount sufficient to attach at least one functional group to a surface of the carbon nanotube.

57. The method of claim 56, wherein at least one functional group comprises a carboxyl group.

58. The method of claim 56, wherein at least one functional group comprises an amine or polyamine group.

59. The method of claim 51, wherein the least one solvent comprises water, an alcohol, or mixtures thereof.

60. The method of claim 51, wherein the suspension is deposited by differential pressure deposition.

61. The method of claim 51, wherein the suspension is deposited onto a carbon based substrate.

62. The method of claim 53, further comprising forming at least one additional suspension, said additional suspension having a ratio of functionalized carbon nanotubes to fibers different from said first suspension.

63. The method of claim 62, comprising forming at least two alternating layers of nanomesh, wherein at least one layer is formed from the first suspension and at least one additional layer is formed from the additional suspension.

64. The method of claim 51, wherein the porous support substrate comprises a sheet or block of a material chosen from ceramic, carbon, metal, and plastic, and a fibrous material, said fibrous material being woven or non-woven.

65. The method of claim 51, wherein at least one molecule or cluster comprises an inorganic compound containing at least one atom chosen from aluminum, selenium, hydrogen, lithium, boron, carbon, oxygen, calcium, magnesium, sulfur, chlorine, scandium, titanium, vanadium, chromium, manganese, iron, cobalt, nickel, copper, zinc, gallium, germanium, bromine, strontium, yttrium, zirconium, niobium, molybdenum, rhodium, palladium, iodine, silver, indium, tin, cesium, barium, lanthanum, tantalum, tungsten, iridium, hafnium, rhenium, osmium, platinum, gold, mercury, thallium, bismuth.

66. The method of claim 51, wherein the cluster comprises quantum dots.

67. The method of claim 51, wherein at least one molecule or cluster comprises an organic compound comprising one or more proteins, carbohydrates, polymers, aromatic or aliphatic alcohols, and nucleic or non-nucleic.

68. The method of claim 51, wherein at least one molecule or cluster comprises an organic compound comprising one or more chemical group chosen from carboxyls, amines, arenes, nitriles, amides, alkanes, alkenes, alkynes, alcohols, ethers, esters, aldehydes, ketones, polyamides, polyamphiphiles, diazonium salts, metal salts, pyrenyls, thiols, thioethers, sulfhydryls, silanes, and combinations thereof.

69. The method of claim 51, wherein said fiber is chosen from:

(a) at least one polymeric material chosen from single or multi-component polymers chosen from nylon, acrylic, methacrylic, epoxy, silicone rubbers, polypropylene, polyethylene, polyurethane, polystyrene, polycarbonates, aramids, polychloroprene, polybutylene terephthalate, poly-paraphylene terephtalamide, poly (p-phenylene terephtalamide), and polyester ester ketone, polyesters, polytetrafluoroethylene, polyvinylchloride, polyvinyl acetate, viton fluoroelastomer, polymethyl methacrylate, polyacrylonitrile, and combinations thereof;

(b) at least one ceramic material chosen from boron carbide, boron nitride, boron oxide, spinel, garnet, lanthanum fluoride, calcium fluoride, glass, quartz, silicon carbide, silicon nitride, carbon and its allotropes, alumina, aluminum hydroxide, aluminum nitride, zirconium oxide, zirconium carbide, hafnium boride, thorium oxide, yttrium oxide, manganese oxide, manganese hydroxide, magnesium oxide, magnesium hydroxide, cordierite, mullite, ferrite, sapphire, steatite, titanium carbide, titanium nitride, titanium boride, zirconium boride, zirconium nitride, and combinations thereof;

(c) at least metallic material chosen from aluminum, boron, copper, cobalt, gold, platinum, palladium, silicon, steel, titanium, rhodium, iridium, indium, iron, palladium, gallium, germanium, tin, tungsten, niobium, manganese, magnesium, molybdenum, nickel, silver, zirconium, yttrium, and oxides, hydroxides and/or alloys thereof; and (d) at least one biological material or derivative thereof chosen from cotton, cellulose, wool, silk, and feathers, and combinations thereof.

70. The method of claim 51, wherein the metal in the metal coated or decorated glass fibers comprises iron hydroxide.

71. The method of claim 51, wherein said fibers comprise metal, metal oxide, or metal hydroxide coated or decorated glass fibers having a diameter ranging from 0.1 μm-5 μm.

72. The method of claim 53, wherein the carbon nanotubes are functionalized to adjust their zeta potential in order to control their attraction to other carbon nanotubes, to particles, to fibers or to combinations thereof.

* * * * *